United States Patent
Brush et al.

(10) Patent No.: US 11,806,579 B2
(45) Date of Patent: Nov. 7, 2023

(54) SPORTS OPERATING SYSTEM

(71) Applicant: Sonador, Inc., Palo Alto, CA (US)

(72) Inventors: William Ancil Brush, San Carlos, CA (US); Emily Jennifer Pye, Los Altos, CA (US); Shivay Lamba, Delhi (IN); Kieran Keegan, London (GB); Rahul Garg, Delhi (IN); John Peter Norair, San Francisco, CA (US); James P. Normile, III, Las Vegas, NV (US); Jonathon G. Neville, Auckland (NZ)

(73) Assignee: Sonador, Inc., Palo Alto, CA (US)

( * ) Notice: Subject to any disclaimer, the term of this patent is extended or adjusted under 35 U.S.C. 154(b) by 0 days.

(21) Appl. No.: 17/477,425

(22) Filed: Sep. 16, 2021

(65) Prior Publication Data
US 2022/0080263 A1    Mar. 17, 2022

Related U.S. Application Data

(63) Continuation of application No. PCT/US2021/050543, filed on Sep. 15, 2021.
(Continued)

(51) Int. Cl.
*A63B 24/00* (2006.01)
*G06F 1/16* (2006.01)
(Continued)

(52) U.S. Cl.
CPC ...... *A63B 24/0062* (2013.01); *A63B 24/0006* (2013.01); *G06F 1/163* (2013.01);
(Continued)

(58) Field of Classification Search
None
See application file for complete search history.

(56) References Cited

U.S. PATENT DOCUMENTS

| | | | |
|---|---|---|---|
| 2006/0136173 A1* | 6/2006 | Case | G01C 22/006 702/182 |
| 2010/0057848 A1* | 3/2010 | Mangold | G16H 20/30 709/203 |

(Continued)

OTHER PUBLICATIONS

International Search Report and Written Opinion for International Application PCT/US2021/050543 dated Jan. 11, 2022.

*Primary Examiner* — Charles E Anya
(74) *Attorney, Agent, or Firm* — Baker Botts L.L.P.

(57) ABSTRACT

In one embodiment, a method includes accessing, by one or more computing devices, user sensor data from one or more wearable sensors on one or more players and optical sensor data from one or more cameras, where the user sensor data includes location data of the player and acceleration data, and where the optical sensor data includes several frames portraying the players and several scenes from an athletic event. The one or more computing devices analyzes, using a machine-learning model, the optical sensor data to identify the players and one or more actions during the athletic event and calculates one or more player metrics for the players based on the user sensor data and the identified actions. The one or more computing devices normalizes the player metrics for the players based on one or more weighted parameters and provides a report to one or more users.

20 Claims, 16 Drawing Sheets

Related U.S. Application Data

(60) Provisional application No. 63/079,424, filed on Sep. 16, 2020.

(51) Int. Cl.
*G06N 20/00* (2019.01)
*G06V 20/40* (2022.01)

(52) U.S. Cl.
CPC ............ *G06N 20/00* (2019.01); *G06V 20/42* (2022.01); *G06V 20/46* (2022.01); *A63B 2024/0009* (2013.01); *A63B 2024/0068* (2013.01); *A63B 2220/40* (2013.01); *A63B 2220/806* (2013.01); *A63B 2220/836* (2013.01)

(56) References Cited

U.S. PATENT DOCUMENTS

| | | | |
|---|---|---|---|
| 2011/0281639 A1* | 11/2011 | Porat | A63F 13/798 463/23 |
| 2013/0045806 A1* | 2/2013 | Bloodworth | G07F 17/32 463/43 |
| 2016/0098941 A1 | 4/2016 | Kerluke | |
| 2016/0220864 A1* | 8/2016 | Hollins | G06Q 50/01 |
| 2017/0173391 A1* | 6/2017 | Wiebe | G16Z 99/00 |
| 2018/0165589 A1* | 6/2018 | Weinberg | G06N 7/005 |
| 2019/0329114 A1* | 10/2019 | Marty | A63B 24/0021 |
| 2019/0366154 A1* | 12/2019 | Callaghan | A63B 21/0724 |
| 2020/0074182 A1 | 3/2020 | Chang | |
| 2020/0134319 A1 | 4/2020 | Ranjan | |

* cited by examiner

SPORTS OPERATING SYSTEM

PRIORITY

This application claims the benefit under 35 U.S.C. § 365(c) of International Patent Application No. PCT/US21/50543, filed 15 Sep. 2021, which claims the benefit under 35 U.S.C. § 119(e) of U.S. Provisional Patent Application No. 63/079,424, filed 16 Sep. 2020, each of which is incorporated herein by reference.

TECHNICAL FIELD

This disclosure generally relates to databases and file management within network environments, and in particular relates to hardware and software for sports analytics.

BACKGROUND

Currently in sports analysis, reviewing hours and hours of film to understand why particular outcomes occur, for example, why goals are scored, through evaluation of team or player performance is exhausting and takes a large number of highly skilled professionals to manually review, tag, extract, aggregate, develop a report, and then visualize the data in such a way to provide meaningful behavioral change. Over the time it takes for this process to occur, the previous game is a distant memory of the past. In addition, there is no platform that provides a player profile to players and teams to better understand the player's performance over time. Players who are extrinsically driven must be expected to dig deep and hope their efforts will help them progress. There is minimal availability of meaningful benchmarking or comparison, such as through data warehousing, to understand how a player matches up against competition. There is currently no integrated product having computer vision synchronized to an integrated wearable solution providing normalized, contextualized data, not currently available in the market. An integrated holistic solution which analyzes, contextualizes, normalizes, provides general- and position-specific ranking and comparison using artificial intelligence (AI) and machine-learning (ML) techniques does not exist.

SUMMARY OF PARTICULAR EMBODIMENTS

Data analytics is revolutionizing sports and insights can be gleaned from the acquired data. Sensor technology and software algorithms can be used to unmask contextual details to assist coaches and players in their respective decision-making processes to ultimately accelerate development and innovation. Fast and accurate information enables dynamic adjustments on the field of play resulting in more positive outcomes.

The "Sports Operating System" framework, described herein, captures an amalgam of sports performance metrics within a single system. Thus, the Sports Operating System may provide a unified performance solution for sports analysis. The Sports Operating System includes a platform, which other applications plug into, that aggregates metadata from a variety of sources to ensure a complete record of the player. As an example and not by way of limitation, the Sports Operating System can be thought of as, among other things, a health system, analyzing as much data on the patient as possible, to ensure optimal health and safety. Furthermore, analyzing an aggregated data set using variables such as climate, rest time, number of games played, number of overall player actions, stress, and using sensor computer vision linked to ID heart rate of a player could greatly impact decision making of player development, valuation, and health safety of players. Being able to collect data from several sources which are soccer specific and contextual using video computer vision to assess overall player ranking, valuation, and health may improve upon the decision making of player development, valuation, and health safety of players. The Sports Operating System may have the ability to leverage computer vision and wearable technology together on a soccer field live. In particular embodiments, video data could be derived from a multi-camera drone to see the entire field of play and be able to zoom in and out based on where the ball is and the intensity of action. The use of video data from a multi-camera drone may lead to obtaining more accurate and engaging player highlights which are vital for making salient coaching decisions.

Particular embodiments include innovation in wearable products and other data collection and presentation products for sports analysis. Biomechanical data capture relies mostly on hardware (e.g., accelerometer, GPS) to collect relevant physical data including, but not limited to, the number of player sprints, top speed, or heat map (e.g., a recording of where the player ran on the field). The mechanisms of wearable technology considered and described herein include GPS which helps to understand where the athlete is running on the field. An accelerometer helps to also understand the change in speed of the athlete in finer degrees than GPS can ordinarily provide. In addition, the wearable device may be worn in the middle of the waist, which may result in a reduction of sports related injuries based on the size and location of the wearable device. The wearable device may be worn in the middle of the waist through lacing the wearable device through the shorts drawstrings, attached to the skin of the waist, and other methods of coupling the wearable device to the user. The positioning of the wearable device at the middle of the body may improve the readings of the wearable device over other wearable devices on t/he market due to the stability of the body at the middle of the waist, the wearable device's fixed location, and small size. Video optical computer vision captures and analyzes event data, which may include, by way of example and not limitation, technical actions of the player like how many shots, how many passes, or how many challenges on the ball. Virtual reality, which may include the use of simulation technology to assist players to better understand tactics, techniques, or become more familiar with an opponent's performance, is integrated as well. Drone technology makes use of autonomous or human-operated flying video cameras to collect data and film on players. Biometric technology may be used to measure sport data closely related to health data, which may include, by way of example and not limitation, heart rate, electrolyte replenishment, respiration, or lactic acid breakdown information, by measuring chemicals in the blood that may facilitate player performance. Bioacoustic data may measure an athlete's voice to provide insight into the readiness of the player.

The embodiments disclosed above are only examples, and the scope of this disclosure is not limited to them. Particular embodiments may include all, some, or none of the components, elements, features, functions, operations, or steps of the embodiments disclosed above.

DESCRIPTION OF EXAMPLE EMBODIMENTS

Figure 1:
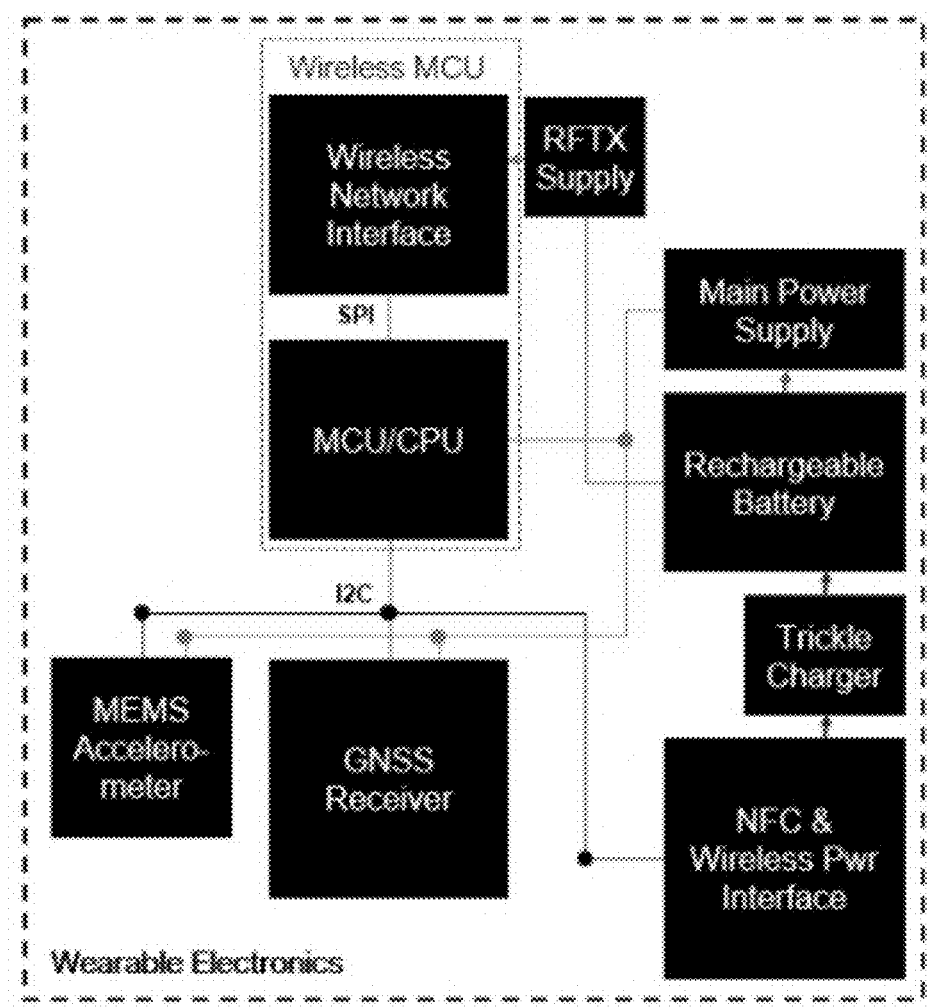
FIG. 1 illustrates an example wearable electronic hardware.

Particular embodiments disclosed herein may be designed to address specific problems or omissions in the current state of the art.

Recent research in wearable hardware suggests that there are limitations to several products available on the market. These main issues of these products pertain to the device's ability to capture reliable acceleration data as well as GPS information consistently. Collecting accurate wearable biomechanical data is paramount for deriving injury preventive data. Current approaches involve determining accelerations to be recorded based upon a universal description of an acceptable "acceleration". This accepted value is typically recorded when a player achieves either a certain speed and or runs at a certain threshold speed for a predetermined distance/period of time. For players of varying ages and body composition this has been concluded to be significantly inaccurate and, therefore, a different method consisting of recording player accelerations is needed. Currently there is no individualized way to continuously and dynamically baseline a player's accelerations as the player grows older and stronger.

Another integral portion of wearable technology is GPS, which has known limitations that arise in certain weather conditions. A cloudy day can alter a player's heat map mobility results, whereas if the day is rainy a player's mobility results may not be visible at all. This impedes a player from having consistent and accurate data to analyze, which prevents them from reaping the rewards of biomechanical data as one must have highly reliable data over a course of time in varying environments in order to properly evaluate themselves holistically. Development of approaches to ensure mobility GPS data is not impacted is also nascent. Today, collected biomechanical data is often not accurate or not consistently collected across time in order to properly analyze a player's performance holistically.

The current market for biomechanical analytics is fragmented. As an example and not by way of limitation, the market includes hardware companies who specialize in products that have GPS sensors tracking location, power, distance, or heat maps. Accelerometer products provide data on shocks, which can be used to show, for example, number of kicks, kick speed, distance ran, or number of sprints. Other approaches generated statistics measuring the effort of the athlete. Still others use radio frequency identification (RFID) local positioning systems or ultra-wide band technology to collect similar measurements. In other environments, optical computer vision is used to collect event data, while some implementations rely on web-scraping techniques to provide analytics and intelligence. Thus while some companies specialize in wearable biomechanical data or video data of team-level events, others provide analytics and insights based on what research is available on the web. There is no system which aggregates these data types for a player, which increases human research time and effort in mapping between databases in order to make comparisons.

Modeling and simulation technology has been used for a variety of different verticals such as flight aeronautics and "what if" scenarios for drugs. However advanced modeling and simulation has not made its way into sports for, for example, performance development. No product on the market can show the consumer a predicted outcome based on previous data, nor has a product emerged which provides decision makers an evaluation of player event data, player physiology, biometrics, player habits, behaviors to predict a player's potential or risk for injury.

The Sports Operating System captures an amalgam of sports performance metrics within a single system. In particular embodiments, the Sports Operating System may access user sensor data from wearable sensors on one or more players, where the user sensor data comprises location data of the player and acceleration data. In particular embodiments, the Sports Operating System may access optical sensor data from one or more cameras, where the optical sensor data comprises a plurality of frames portraying the one or more players and a plurality of scenes from an athletic event. The Sports Operating System may request for data from various sources, such as the wearable sensors or cameras. In particular embodiments, the wearable sensors and cameras may be configured to automatically send data to the Sports Operating System. Particular embodiments include innovation in wearable products. In particular, a buckle design was specifically designed to facilitate accurate sports data collection through a buckle-like form factor fitting through the laces of the drawstring at the waist of the player's shorts, pants, or skirt, which research shows to be the most accurate placement for sports wearable technology since this is the part of the body which is most fixed within movement. Thus the wearable technology may collect and render accurate data and be more comfortable, and possibly unnoticeable, due to its form factor around the waist feeling nearly invisible and unobstructed to the athlete. In addition, the shape of the buckle is such that the ends are hollowed out to absorb shock from being hit by the ball in this area of the body, thereby preventing injury.

In particular embodiments, computer vision also may be synchronized and integrated within the system and wearable device. This functionality may play a large role in the analysis of player actions and performance capabilities of a player. In particular embodiments, the Sports Operating System may analyze, using a machine-learning model, the optical sensor data to identify one or more players and one or more actions during an athletic event. Using proprietary machine-learning algorithms which are contextual for player positions. The contextual nature of the algorithms is one differentiating factor since each position has been normalized by weighting metrics and statistics by their role and responsibility, yielding insights into the degree of talent and performance of each player. The performance of a player can be based on their actions, captured in video, against actions of other players of the same, age, level, position, etc. The same approaches can be used to benchmark the player against more talented players or those who are of similar ability level. In particular embodiments, the Sports Operating System may calculate one or more player metrics for a player based on the user sensor data and the identified actions. The Sports Operating System may also use third-party data sources to calculate the player metrics. This level of analysis may provide particular benefits to the scouting and recruiting market. These algorithms are the result of data science around reviewing player data of several hundred players to determine the most salient statistics correlating with player success per position. In particular embodiments, these key metrics were regressed and then clustered. In particular embodiments, these key metrics were determined utilizing unsupervised learning techniques. To further refine the key metrics, subject matter experts calibrate the stats to determine the weight and true value of the stats. This normalization model helps to ensure data is contextual, meaningful, and objective in a way which can, in itself, screen and compare talent. In particular embodiments, the Sports Operating System may normalize the calculated player metrics based on weighted parameters and other player metrics corresponding to other players.

In particular embodiments, through discussing with the top scouts and coaches in the country key statistics were determined for the different positions of football players. Through this, a ranking system has emerged which can predict which player is better than other players per position. Since the stats are role based and showcase the amount of impact a player has on the game against their peers, the ranking system can devise which player may be better than other players in a specific game across these positions. Each position has a customized algorithm to assist with the data being scored automatically and objectively. The algorithms also compare players within an age group within a position, and in particular embodiments, based on who outplayed who on the team each game. As discussed herein, the same techniques can and should be applied to other sports in order to help measure success and compare players. The Sports Operating System may be used to quickly determine a player's ability level for analysis by the player, coaches, and scouts. The computer vision (CV) tools are used in combination with wearable technology to assist with this process. The boot may be capable of driving the entire process itself. Through the technology of the Sports Operating System, all metrics determined from video may also be determined from the boot, and in addition through using proximity and Sports Operating System HWEye AI Technology may be able to see a player using hardware as if they were using video given any situation within a game.

In addition to ranking metrics using algorithms, embodiments include a model for determining how much each statistic is worth. This algorithm is also position specific and based on a similar process used via data science. This is very important for the professional sector because the professionals which invest in a player want to know whether or not the player has met a certain expectation or are living up to the amount spent or are outperforming their mark. When this happens and an athlete is significantly outperforming based on the amount of money being spent a club can sell the player for much more than what they paid. The TruValu algorithm assists with this and can lead towards identification of diamonds which can be resold at a much higher value. Scouting may use the Sports Operating System for information on how much players should be valued at based on their data and also want to understand their rank.

The motivation behind position specific metrics is balancing science and art. The science of player impact points towards a player's role and responsibility being the most important factor to evaluate a player overall. A forward is rewarded for scoring goals. A defender is rewarded by not allowing goals to be scored, a midfielder is rewarded by being a play maker, and a winger is rewarded by being a player who can beat players one-on-one (e.g., in a "duel") and serve a cross or get on the end of a last pass. It is important to identify what metrics lead towards a position being successful against their peers. This is accomplished through data science methods. Once this is complete, in particular embodiment, human analysts balance, validate, and calibrate the metrics. The data helps steer the system in a direction and then the human analysts, based on the data, make important tweaks to ensure the metrics are weighted in a way which may add the most value possible. This is then built into the CV tools and by using algorithms determine a player's performance and predict future outcomes based on previous data studies and algorithms which can predict future outcomes and performance levels. It is important for an athlete to know what the future may hold if they stay with a certain path or if they make changes how this may change their future based on their peers at a given point in time.

In particular embodiments, the Sports Operating System platform may be a software system hosting a community of players, coaches, and scouts accessing data on each other which is accurately harvested through data collection/harvesting products like wearables, uploading videos with computer vision, and or aggregating other devices or data from third party application programming interface (API) metadata to properly assess an athlete's and team's performance. The Sports Operating System platform also enables external developers to build and deploy applications which integrate into the system. The Sports Operating System encourages the world to develop wearables and technologies to support athlete development and monetize their own applications via the Sports Operating System. In addition, to computer vision, augmented reality applications include enabling a more powerful experience for players to gain knowledge through observation and engagement within the learning process. Lastly, through development of drone technology, several camera angles can be combined through the use of AI which captures video and performance metrics in an optimized manner for data accuracy. These drones know where each other are in real-time and through the use of AI move around each other spatially following the run of play maintaining a triangular shape equidistant from each other at all times. Thus drones may enable higher quality video, better camera angles, faster processing, and greater accuracy of data capture and data analytics for end users. The Sports Operating System also enables peer to peer messaging from a player to player, player to their coach or other coaches, and player to scout has been built and may further accelerate the developmental process of athletes, coaches, and scouts through virtual coaching and or connecting with players more easily which have been provisioned through AI techniques which account for players which suit a particular scout or coaches needs best. The Sports Operating System may also provide a report to one or more users about the normalized player metrics of a player. The reports may be available to other users based on a permission given to the users from the player associated with the respective report. In order to tie everything together the system would not be fully complete unless there was an opportunity to agree on terms from both the athlete and the owner of a club. In particular embodiments, the Sports Operating System may enable a seamless contract agreement which is completed securely, legally, saving time, money, and opening the world up to a new way to shop for athletes based on accurate data analytics.

In particular embodiments, in addition to soccer, the same techniques can be applied throughout the sports industry. As an example and not by way of limitation, applications to American football can involve reviewing who are the top football players and why. Since this sport is heavy around injury, the injury index described herein, which is yielded after every match, would be very helpful. Every sport has the same problem with youth around the world. Most sports focus on only professionals, neglecting tools for the player who wants to become a professional athlete or wants to understand what it takes to become one. In particular embodiments, techniques described here may become standard across the entire sports industry as a virtual rolodex of athletes who can search each other (subject to privacy settings).

In particular embodiments, analytics through the Sports Operating System may also be helpful for warehouse workers who need to best estimate how much work will be needed in order to complete a job. A person will not need to go and count boxes, instead embodiments of the Sports Operating System may be able to use computer vision technology to estimate how large jobs are, how much, and provide immediate estimates to improve the amount of time and cost it takes to move shipments of any type of goods.

In particular embodiments, in the arts and music industry, the Sports Operating System can be applied, for example, by being able to sort through musicians to provide information on the pitch and quality of sound/voice in an automated way instead of having an actual trainer who is training the composer and or actor. Music via dance, voice, and acting can be scored immediately and depending on the quality can put actors with certain types of agencies who are looking for certain levels. The Sports Operating System removes the need for subjective judges by providing objective feedback and then linking the types of musicians/artists/actors with the type of agencies which would be interested. Since the Sports Operating System supports an ecosystem of scouts, the musicians have immediate access as well like never before.

In particular embodiments, the Sports Operating System uses APIs and encourages an open operating system framework encouraging additional external users to develop on-top of the framework of the Sports Operating System. These updates, which come from an external developer, may be under a controlled environment with specific tools for development, or, will go through a submission process which will be integrated internally. Role-based access may be introduced to ensure privacy is closely governed. Players may be able to control who may see their information (e.g., via user preferences or privacy settings), and coaches and clubs may be able to implement policies which may enable or disable access to their player's data. Scouts as well, may be able to control who can see their data. Blockchain technology may be utilized to improve security and reduce the potential for data vulnerability. The privacy settings system may allow athletes to provide visibility to the coaches and scouts with which they wish to communicate. The coach may first register and then players may register by authenticating through the coach. If the player register individually a two-step authentication can be imposed to ensure access to the system via client and wearable is controlled for the safety of the athlete. APIs may further provide for specialized security solutions for different use cases (e.g., a local player-fan relationship may be different from a scout or fan accessing a superstar).

System features of software, AI, & computer vision may include:

Automated clipping of player actions: When a player action is learned via ML this action records the action, aggregates the total number, and then automatically clips and stores each action. Thus, each action, e.g. if there are 5 shots, may be automatically recorded and accompanied by their highlights or video. At the time of each action recorded embodiments may provide the preceding period of time, e.g., 5 seconds, or following period of time, e.g., 3 seconds, to show the build-up and the impact of the action.

Object detection

Facial recognition may enhance the detection of respective athletes. Moreover, machine learning may enhance the ability to recognize and judge a player's ability within a significant confidence level by reviewing the facial profile and body physique for specific sports to include such as soccer, basketball, football, lacrosse, baseball, cricket, golf, ice hockey, volleyball, swimming, tennis, and boxing.

Goal detection and minutes played are two very important stats which are critical pieces and constants of the game.

Tracking performance event data: Each player action recorded by video in the game/practice is called event data. Machine learning may record and aggregate each event data stat automatically Automated ranking player performance: Based on each action using algorithms and machine learning models to learn positions, and weights of actions, these actions may be recorded as a difficulty, and as the game moves on automatically may be able to know which actions have a higher difficulty and automatically rank these actions and their end performance. This may be based on a number of factors like the level of play, how many players are surrounding the athlete, their orientation, how many teammates options are around the teammate, where the player is on the field, etc. Thus, the player ranking component can situationally analyze and rate a performance action.

Future predictive performance ranking: Based on previous game analysis and an understanding of the competitor, the system may be able to automatically predict each performance metric which an athlete should be able to achieve. This may greatly assist as inspiration to the athlete to beat their predicted statistics.

Tracking spatial data

Tracking sequencing of plays: Based on machine learning models, the system may be able to automatically share how many times a certain play happened and show each of these. In addition, show only the plays/video highlights which the athlete was involved in during the game both on offense and also on defense Displaying individual player clips associated only with individual players instead of the entire match automatically Detecting if a player has an injury: This may be achieved in two ways. First, building an injury index into the wearable technology and understanding how much an athlete weighs and the body composition as height, along with the athlete's speed may be able to understand the amount of energy and power on an athlete's joints. This is also known as load. An athlete should not be spending a certain amount to load/time in the red zone and when this athlete gets close to this zone the coach can be notified. At the end of each match a player can be provided with an injury risk prevention index via the wearable technology. Second, watching the athlete extremely closely with machine learning and learning what actions lead towards an athlete having an injury may be able to detect movements as risks which immediately trigger and inform the coach.

Longitudinal (acute-chronic workload balance) and the retrospective (performance change). Analyzing body composition, height, weight, along with stress on joints via number of sprints, duration, intensity, along with field type and environmental conditions. The Sports Operating System may benchmark the athlete themselves within the given sport context as well as other players who are similar to them based on body composition, speed. etc. and against the players who are having these injuries. In addition, when injuries happen the Sports Operating System shall annotate these, store, and further assist with making better predictions based on the data collected.

FIG. 1 illustrates embodiments of wearable electronic hardware including the following components:

Microcontroller computing unit (MCU), to run application firmware and facilitate interactions between sensors, input/output (I/O), and power systems.

Wireless network interface, implemented as a wireless transceiver integrated circuit (IC) that communicates with the MCU via a wired data bus such as serial peripheral interface (SPI), for the purpose of sending telemetry and receiving control information.

GNSS receiver, implemented as a wireless receiver IC that communicates with MCU via a wired data bus such as inter-integrated circuit (I2C), for the purpose of receiving and interpreting transmissions from GNSS satellites.

Micro-electromechanical system (MEMS) accelerometer, implemented as a sensor IC that communicates with MCU via a wired data bus such as I2C, for the purpose of measuring 3-axis (X/Y/Z) accelerations.

NFC and wireless power interface, implemented as one or more ICs that communicate with MCU via a wired data bus such as I2C, for the purpose of interfacing with external NFC devices (e.g. smartphones) and also for the purpose of collecting power transferred wirelessly via a compatible wireless power transmitter.

A trickle charger, implemented as an electronic circuit, for the purpose of converting the power received via the wireless power interface to a voltage level useful for charging an integrated battery.

A rechargeable battery, nominally utilizing a lithium-polymer technology, which is charged by the trickle charger (6) and which supplies all electric power required by the system's electronics.

A main power supply, implemented as an electronic circuit, which outputs a stable voltage to system electronics and has a variable battery voltage as input.

A secondary power supply, implemented as an electronic circuit, which outputs a stable voltage different from the voltage supplied by the main power supply (8) and has a variable battery voltage as input. Secondary power supply is specifically utilized for powering the radio-frequency (RF) transmitter amplifiers, and it is specified to meet the requirements of the selected RF transmitter amplifiers.

In particular embodiments, the system may use a mobile network. The mobile network may include a central unit, hotspots, peripherals, and cloud services. The central unit may be embodied as a tablet. The hotspots may be embodied as a smartphone that provides cloud access and live data streams. The peripherals may be embodied as other devices. The cloud services may include game analysis, remote tracking, player performance metrics, and parent subscriptions.

Figure 2:
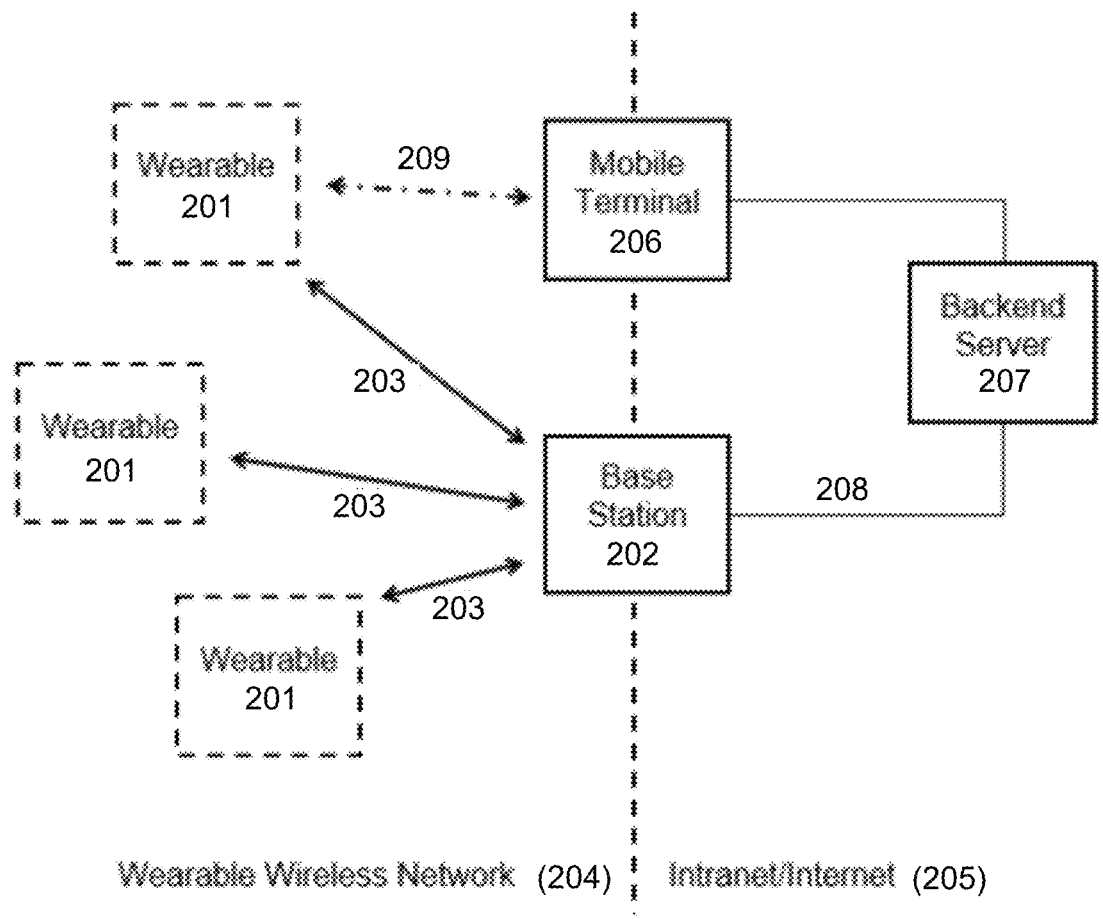
FIG. 2 illustrates an example embodiment of a proposed workflow.

Particular embodiments disclosed herein may be implemented using one or more example processes. FIG. 2 illustrates an example embodiment of a proposed workflow.

The Sports Operating System may optionally utilize a wearable, electronic device ("wearable") as a means of measurement input.

In particular embodiments, the Sports Operating System may comprise one or more wearable devices 201 and one or more network base stations 202. The role of the network base station 202 may includes receiving telemetry from connected wearables via one or more connections 203, sending control data to wearables via the connections 203, caching data received from the network of wearables, converting data formats of the data received from the network of wearables into data formats ingestible into other components of the Sports Operating System, communicating with a second network on which other components of the Sports Operating System are connected. An exemplary embodiment of said second network is the Internet.

In particular embodiments, the base station 202 may be an electronic device of exemplary embodiment similar to that of a WI-FI router. It may contain a primary wireless network interface 204, which may be used to communicate with wearables. In particular embodiments, it may contain a secondary network interface, which may used to communicate with the internet or local LANs 205. It may utilize a CPU and memory for the purpose of executing embedded software doing the task of routing and processing information between the primary and secondary networks.

In particular embodiments, the Sports Operating System implementing wearables also may include one or more mobile terminals 206. As an example and not by way of limitation, the mobile terminals 206 may include one or more near-field communication (NFC)-enabled smartphones.

In particular embodiments, the Sports Operating System may also include one or more backend servers 207 accessible via the internet or a local intranet, through application protocols built-on Internet protocol stacks 208. The base stations 202 may shares the information they collect from wearable devices 201 with the backend servers 207.

The wearable devices 201 may be embodied in a plurality of form-factors, including but not limited to a boot-mounted enclosure, a waistband-mounted enclosure, an adhesive-backed skin-mounted patch, and other suitable embodiments.

The wearable devices 201 may implement an electronics system including a microcontroller which communicates with and controls subsystems using an electrical signaling bus. The bus may utilize any suitable technologies, including but not limited to raw digital I/O, raw analog I/O, SPI, I2C.

The wearable devices 201 may implement a rechargeable battery with integrated charging features. The battery may be charged using a direct, wired connection to DC voltage, or a wireless charging receiver. Wearables utilizing a wired charger may include a connection port capable of mating with a corresponding wire connector. An exemplary embodiment is a USB cable. Wearables utilizing a wireless charger must implement a wireless charging receiver. An exemplary embodiment is an NFC transponder with energy transfer features.

The wearable devices 201 may implement one or more sensors or receivers including, but not limited to: Global Navigation Satellite System (GNSS) receiver, wireless real-time location systems (RTLS) receiver, accelerometer, gyroscope, temperature sensor, heart-rate sensor, galvanic skin response sensor, and any other suitable sensor.

The wearable may implement a far-field wireless transceiver. The far-field wireless transceiver may implement one of a variety of technologies, including but not limited to: WI-FI, BLUETOOTH, LTE, Global System for Mobile Communications (GSM)/General Packet Radio Services (GPRS).

The wearable devices 201 may implement a near-field wireless transponder. An embodiment of the near-field wireless transponder is a standardized, NFC transponder. The role of the transponder is to communicate directly with a mobile terminal at very short ranges, on the order of 10 cm. The short range may implicitly guarantee a 1:1 connectivity between the said mobile terminal and a single wearable.

The wearable devices 201 functional mode of operation is to take measurements from its suite of integrated sensors and receivers, processes them using integrated signal processing resources, and transmits the processed measurements to the base station via its far-field wireless transceiver. A function of systems including the base station and wearable is to propagate telemetry generated on the wearable into equivalent data residing in an internet database in "real-time". In particular embodiments, "real-time" may be quantified to mean less than 100 ms. The wearable itself may use cellular technology to automatically send data generated by the wearable. All implementations of the wearable including the boot, patch, buckle, clip, and the like may use cellular technology. The wearable devices may have a magnetometer which may enable outdoor transmission of data to the cloud and is also usable within indoor sports areas, such as areas for basketball, football, baseball, hocket, etc. The magnetometer may detect magnetic forces which may be used to determine positioning after calibration of the field size parameters. Consuming the vast spectrum of data points from a wearable and synchronizing with computer vision video, personalized data like banking, sleep, nutrition, can lead to very specific decisions tailored towards human growth and performance by the player. This consumption of data can also lead towards scouting and coaching decisions. The context of each individual sport may lead towards different decisions even if data may be similar. For instance, if two seventeen-year-old males who have the same socio-economic background with similar nutrition and sleeping patterns play two different sports (e.g., football and soccer), then different decisions may be generated based on the data accumulated for each individual player. Obtaining benchmarks and using data science algorithms to compare each individual sport is key in order to prescribe appropriate methods and training strategies which lead towards performance growth, safety, and healthy. In order to save coaches time, the Sports Operating System may have the ability to couple the top communication media (e.g., text, messenger, social media) and may lead to suppressing certain messages which are not as important or even providing an auto response based on behavior. And messages from coach leadership and players or prospective players may be provided message filtering so to not interfere with coaches and scouts workflow. The volume of noise (e.g., unnecessary communication) may be a primary pain point that slow coaches down. The players that are shown to the coach may be based on their behaviors previous interests, culture, value, and organization budget. The message handling may lead to a decrease in waste and increase of cost effectiveness, saving time and money.

A wearable devices 201 may be added to a base station's 202 network via commands sent downstream from a base station 202 to a given wearable 201, using the far-field transceiver as means of communication. The invocation of these commands may be based on automated software running on the base station itself or from external sources which may trigger the base station to add one or more wearables to its network.

A wearable devices 201 may also be added to a base station's 202 network via commands sent downstream from a mobile terminal using the near-field transponder communication means 209. In this embodiment, necessary information pertaining to the connection of the given wearable to a given base station must be known by the mobile terminal and conveyed from the mobile terminal to the wearable.

Figure 3:
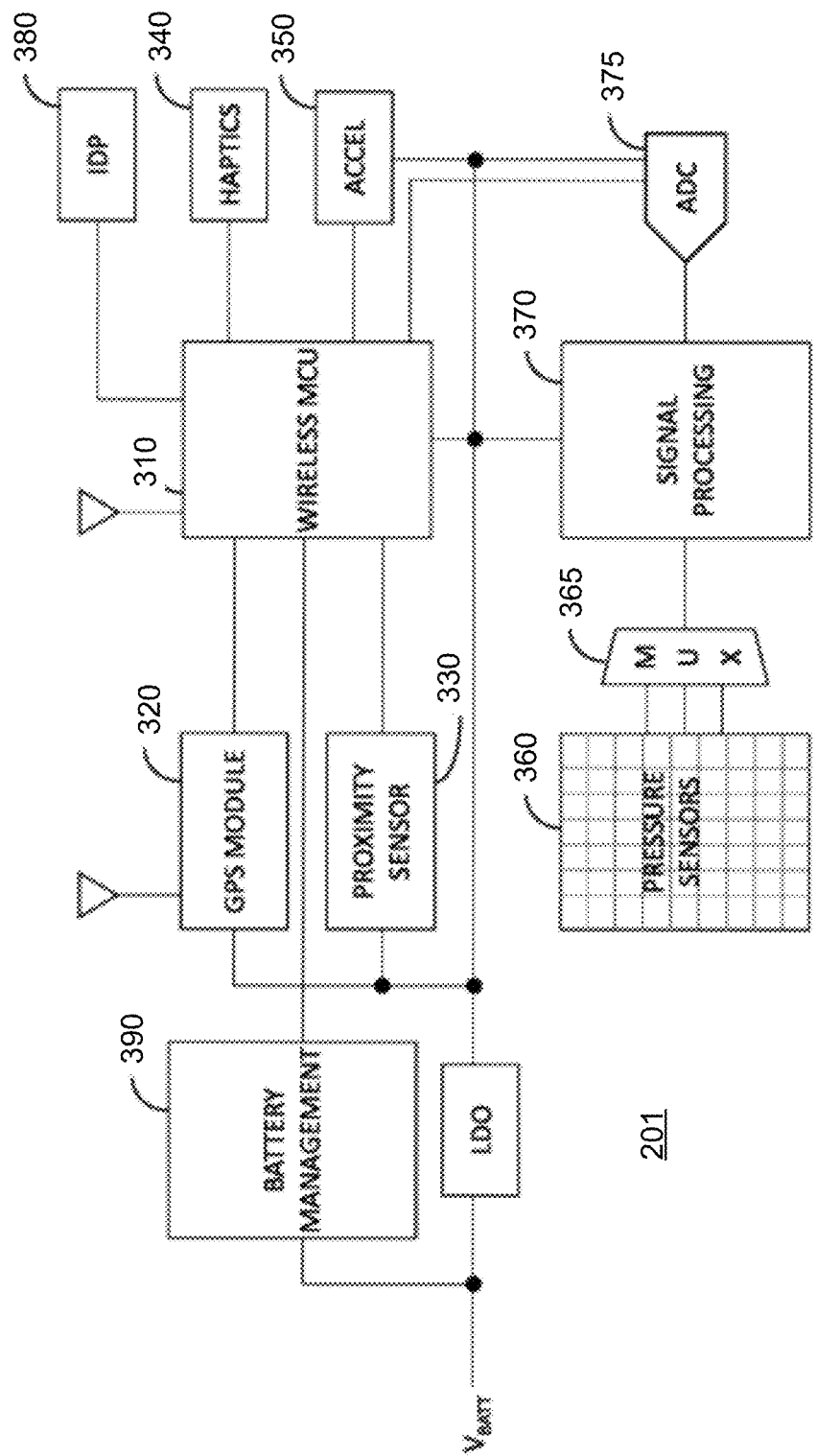
FIG. 3 illustrates an example block diagram of a wearable device.
Figure 4A:
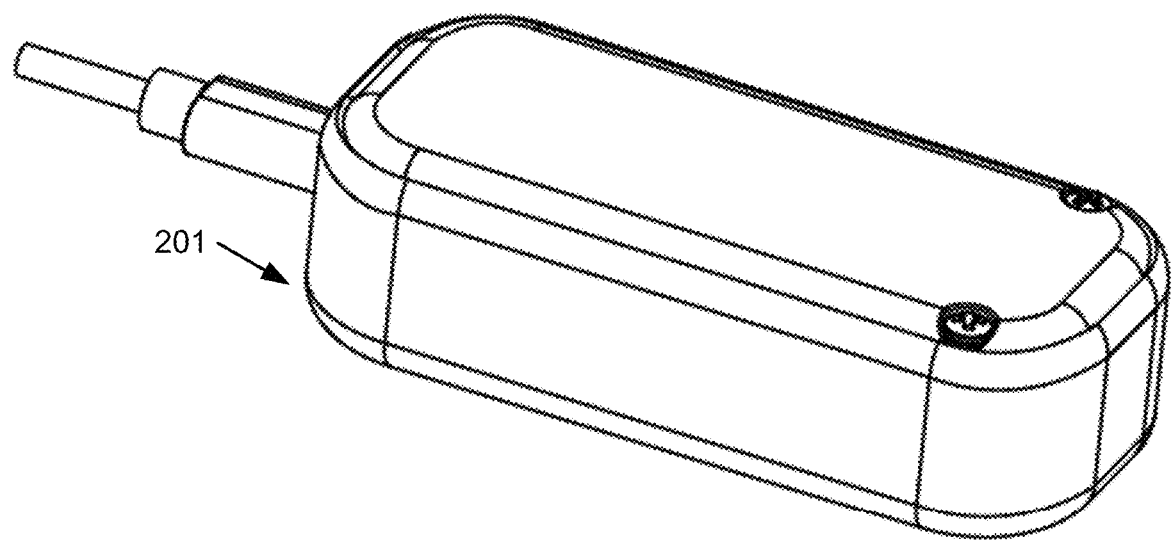
FIGS. 4A-4E illustrate an example embodiment of the wearable device.
Figure 4B:
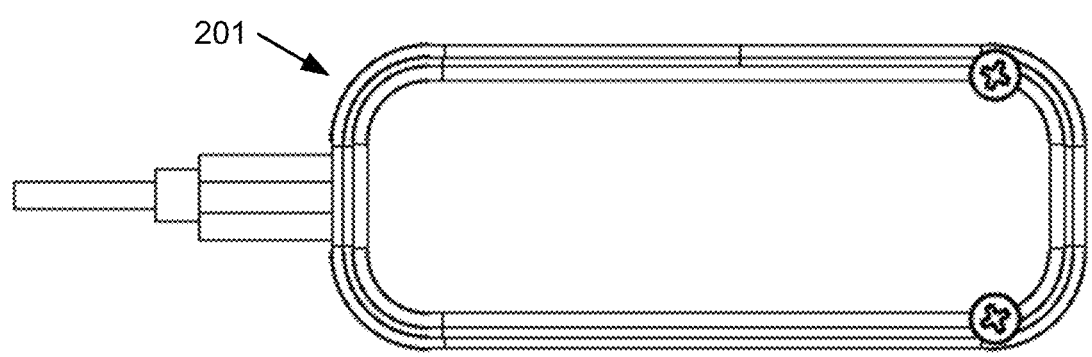
Figure 4C:
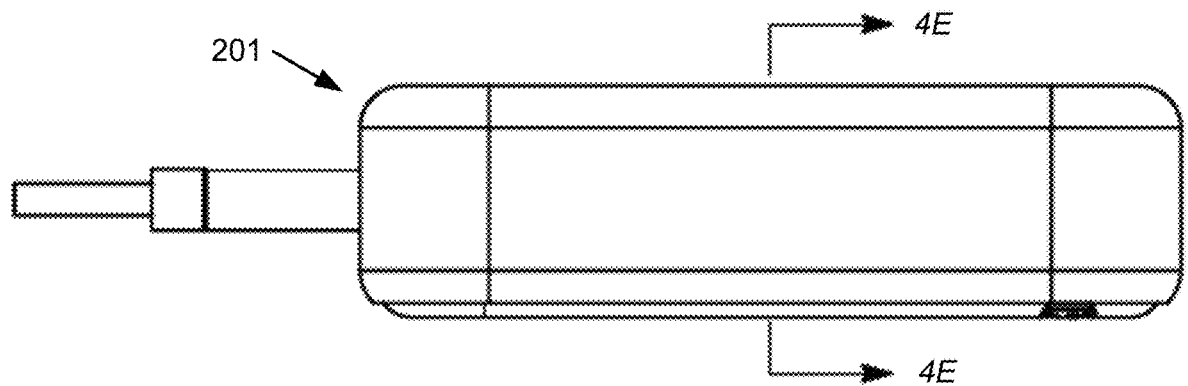
Figure 4D:
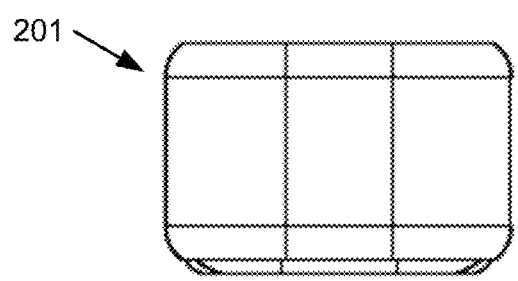
Figure 4E:
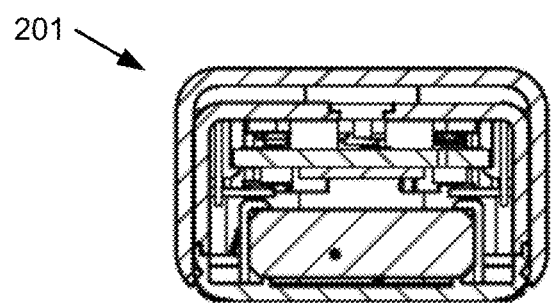
Figure 5A:
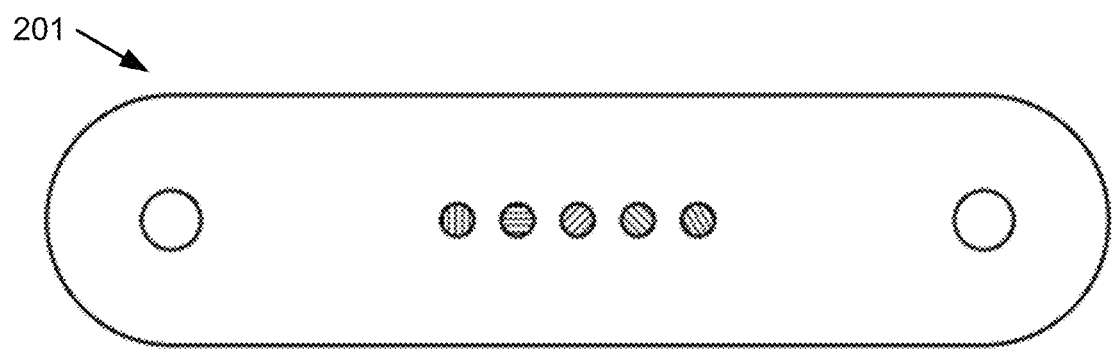
FIGS. 5A-5C illustrate an example wearable buckle embodiment of the system.
Figure 5B:
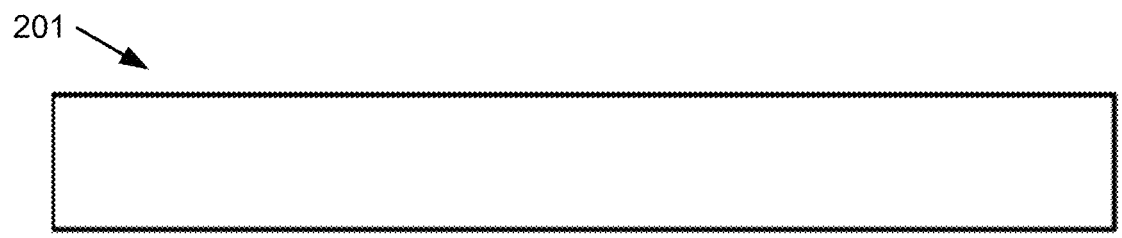
Figure 5C:
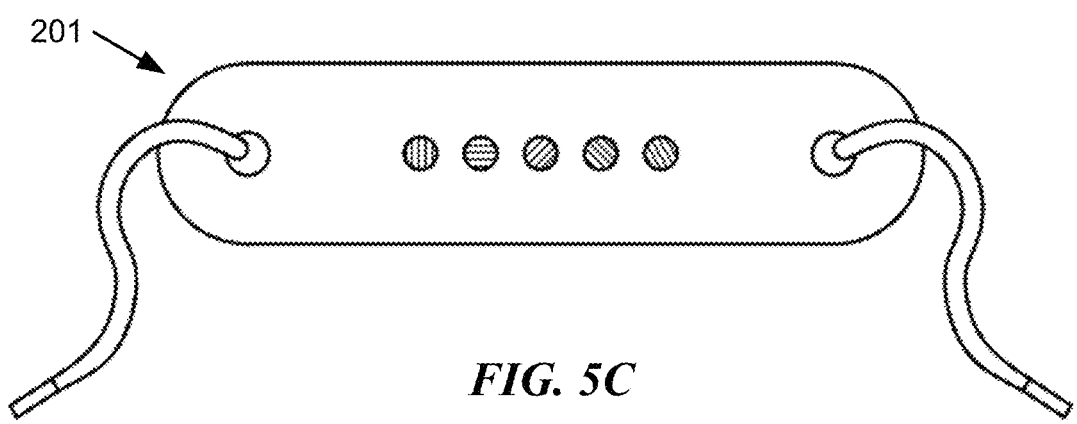

FIG. 3 illustrates a block diagram of an example wearable device 201. Microcontroller unit (MCU) 310 may receive input signals from one or more sensors and other modules, such as, by way of example and not limitation, GPS module 320, proximity sensor 330, haptics module 340 (which may include a tactile sensor and a feedback mechanism), accelerometer 350, and pressure sensor array 360. In particular embodiments, the pressure sensors in array 360 may be arranged in groupings corresponding to a plurality of surfaces covered by the wearable device, and the input signals from pressure sensor array 360 may be transmitted through multiplexor 365 to signal processing unit 370. In particular embodiments, one or more of the input signals may be pre-processed using analog-to-digital converter 375 (as needed). In particular embodiments, signal processing unit 370 may amplify one or more of the input signals. Wearable device 201 may further perform optimization functions on the input signals, such as denoising, smoothing, interpolation, extrapolation, etc. using signal processing unit 370 or MCU 310. Wearable device 201 may also provide feedback to the player using an IDP module 380 (which may provide feedback using haptic feedback, audio feedback, visual feedback, or any other suitable manner). Wearable device 201 may also include a battery management system 390, which may provide power using a battery pack, intelligently conserve power as appropriate, or recharge the battery pack (e.g., using a mechanism to capture the player's kinetic energy or solar cells). In particular embodiments, wearable device 201 may further include a networking component to transmit data in real time to the gateway device using, by way of example and not limitation, BLUETOOTH LOW ENERGY, WI-FI, or a mesh network.

FIGS. 4A-4E illustrate an example embodiment of the wearable device 201. The wearable device 201 may include the features of a wearable device 201 as described herein. The wearable device 201 may aggregate data holistically and individually specific to a baseline and then consistently understand how the player evolves, which may be important for player, coach, and scout.

Figure 6:
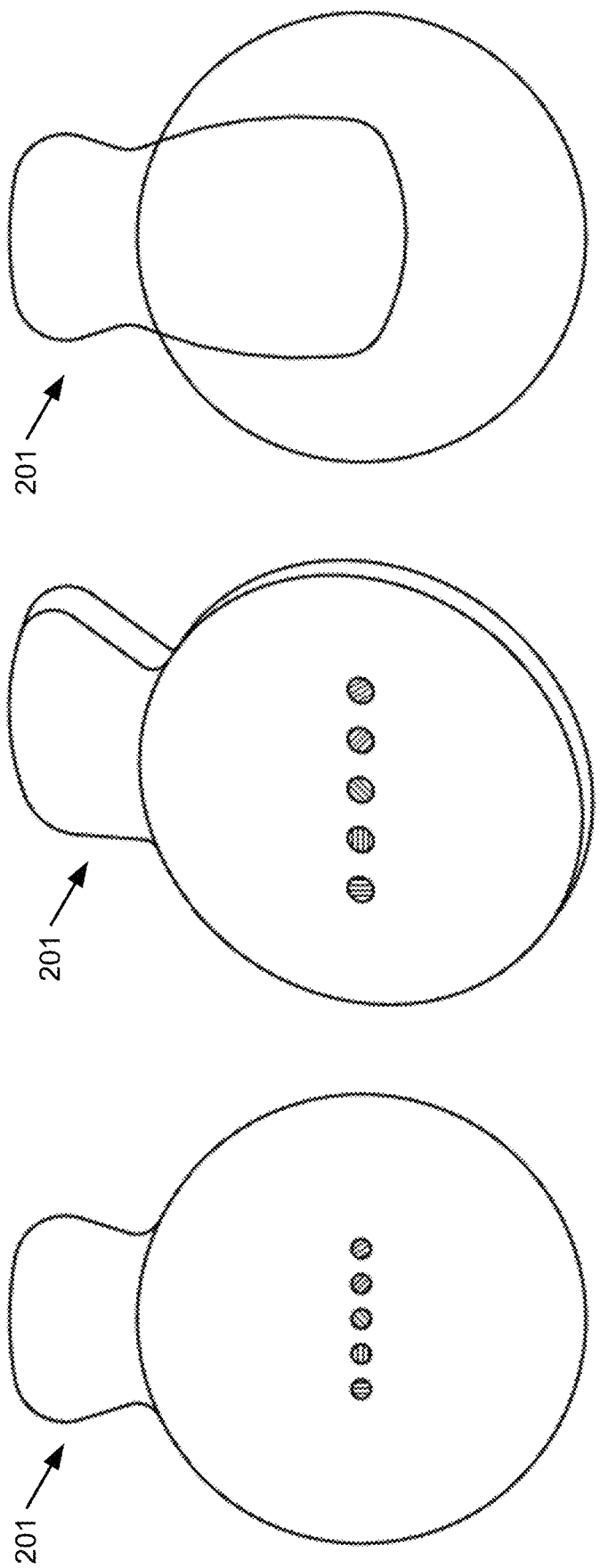
FIG. 6 illustrates an example waist band clip embodiment of the system.
Figure 7A:
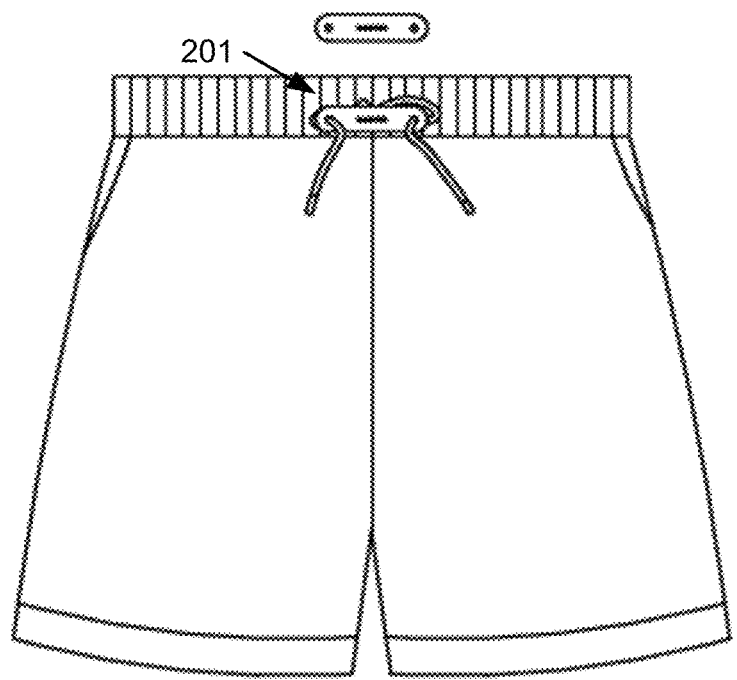
FIGS. 7A-7B illustrates an example embodiment of the system.
Figure 7B:
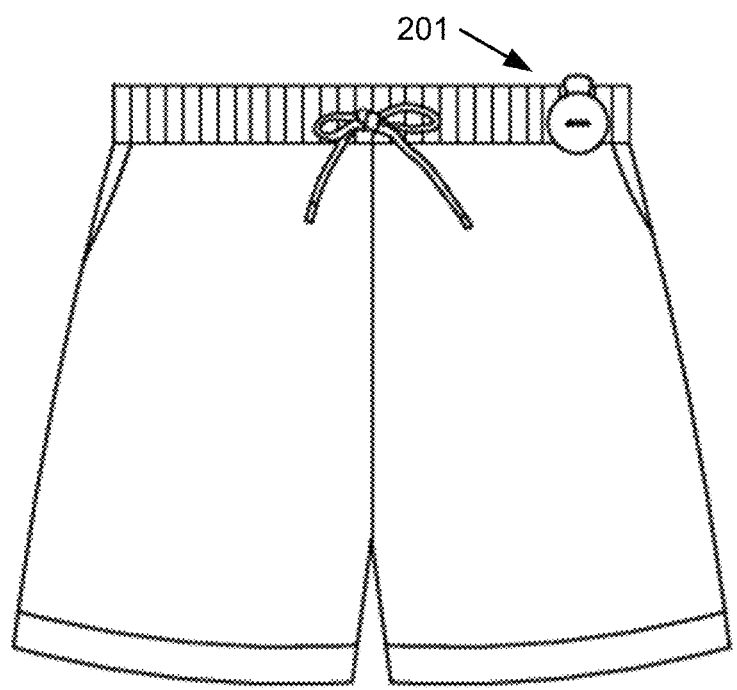
Figure 8A:
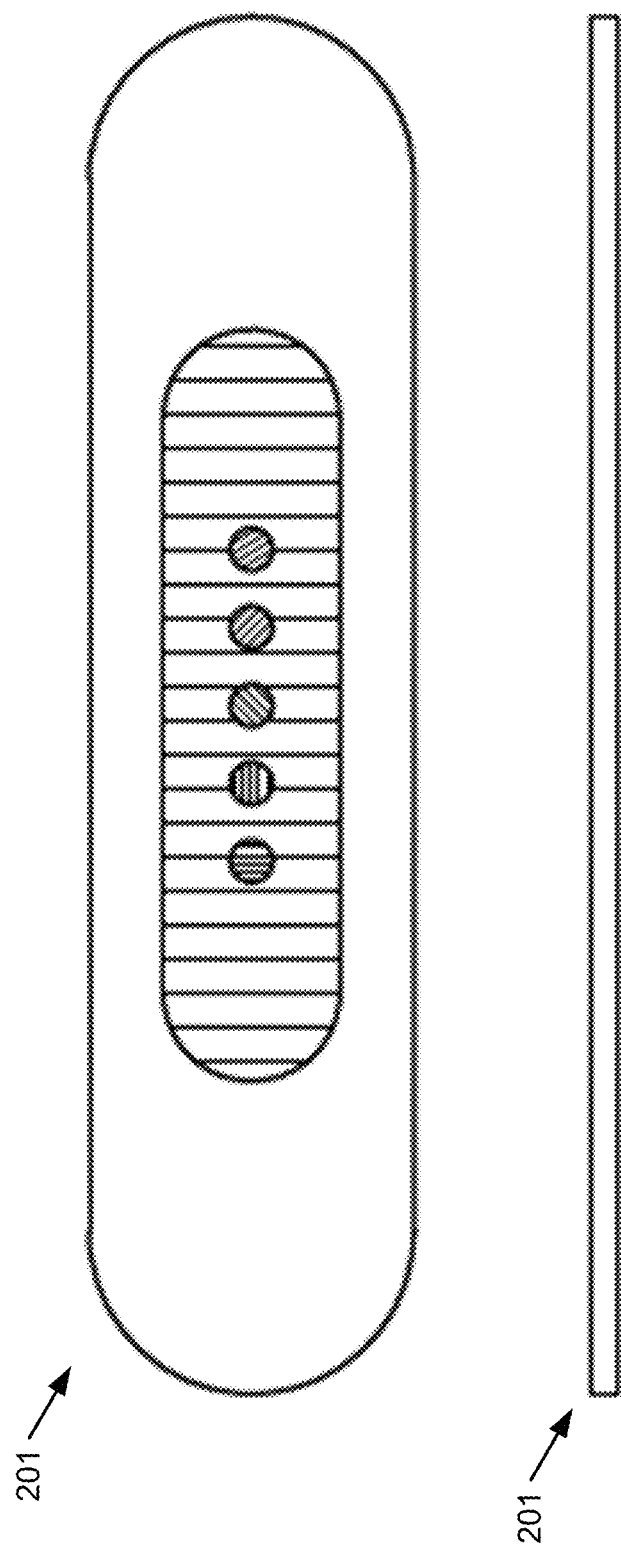
FIGS. 8A-8C illustrate example embodiments of the system.
Figure 8B:
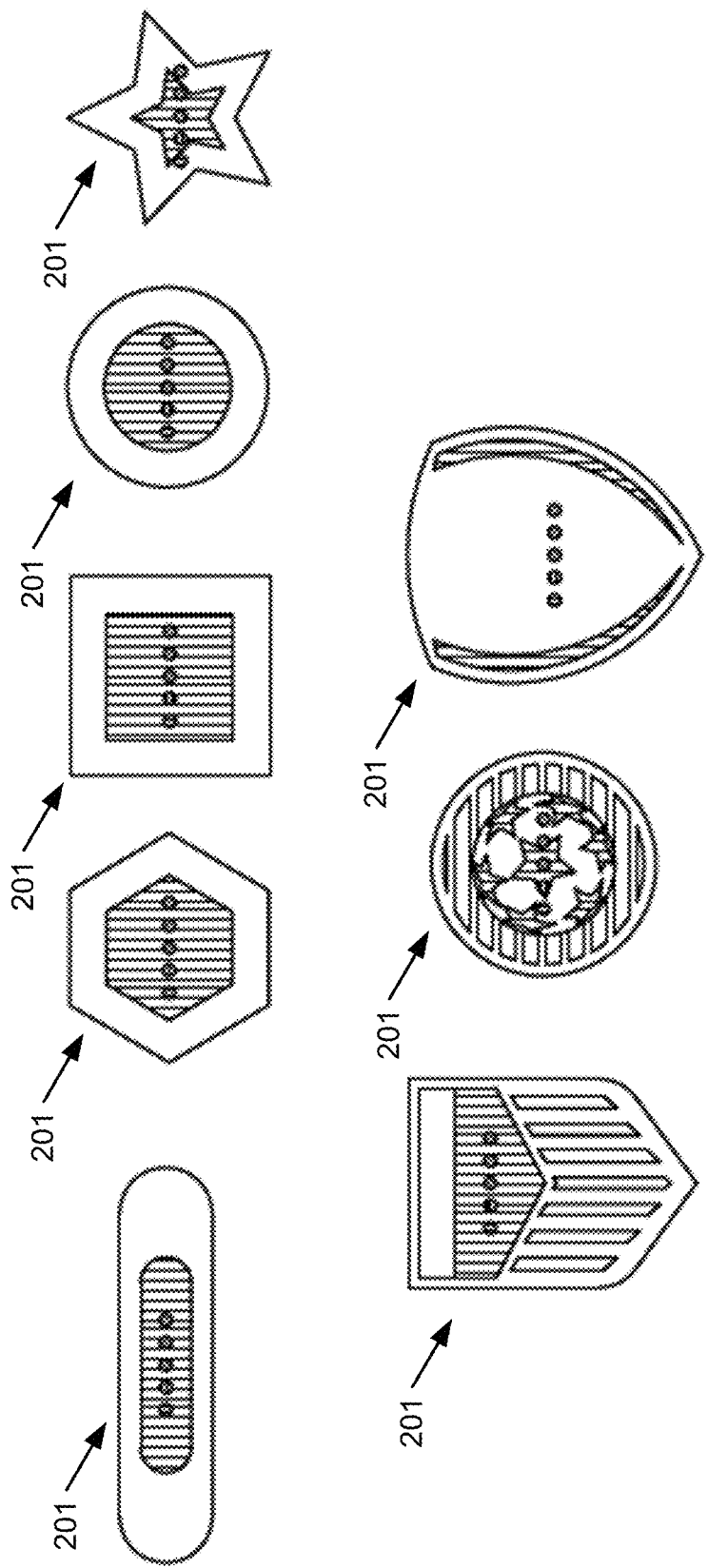
Figure 8C:
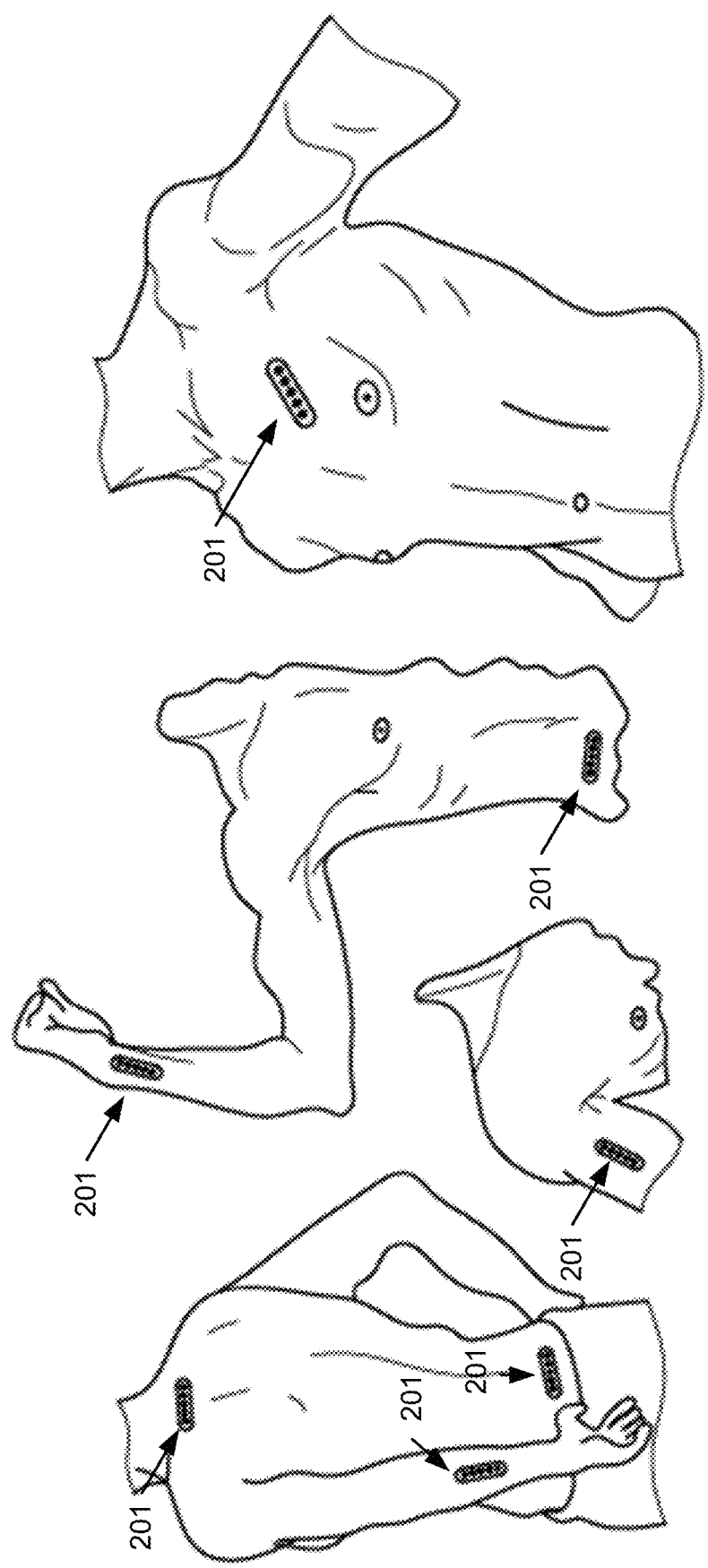
Figure 9:
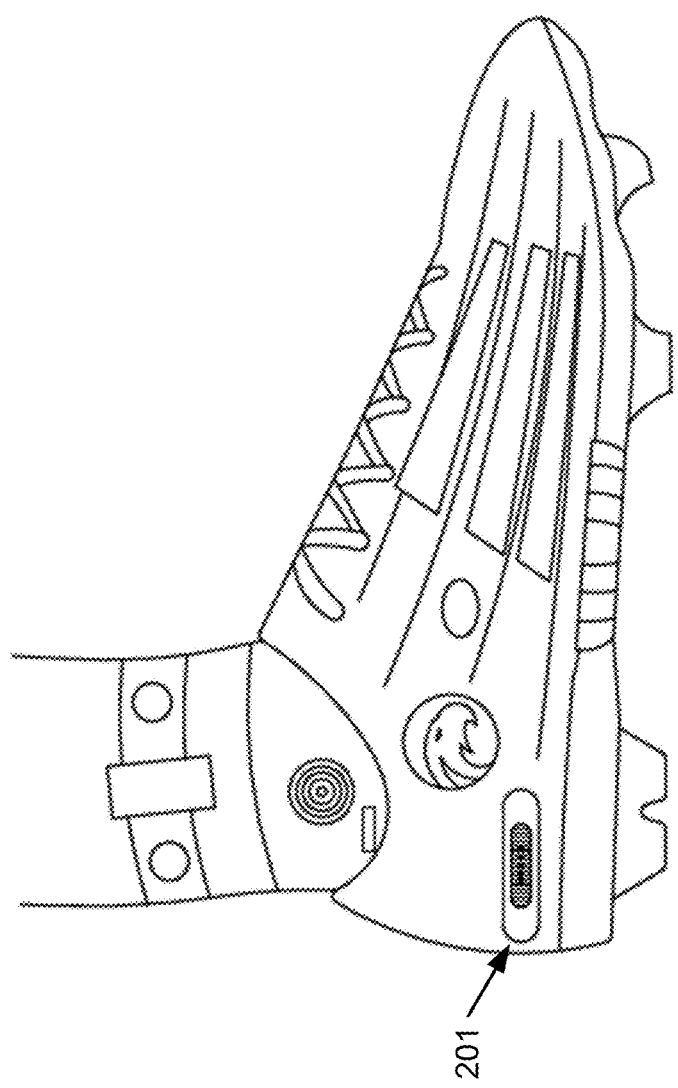
FIG. 9 illustrates an example wearable boot embodiment of the system.
Figure 9:
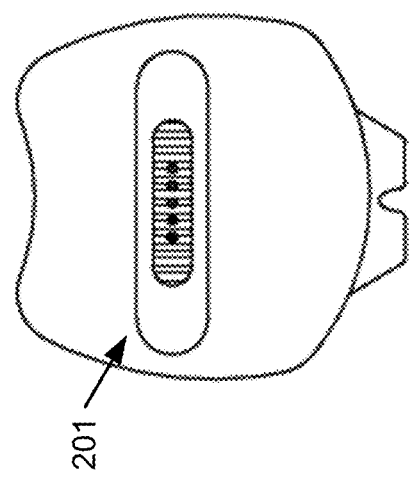
Figure 11:
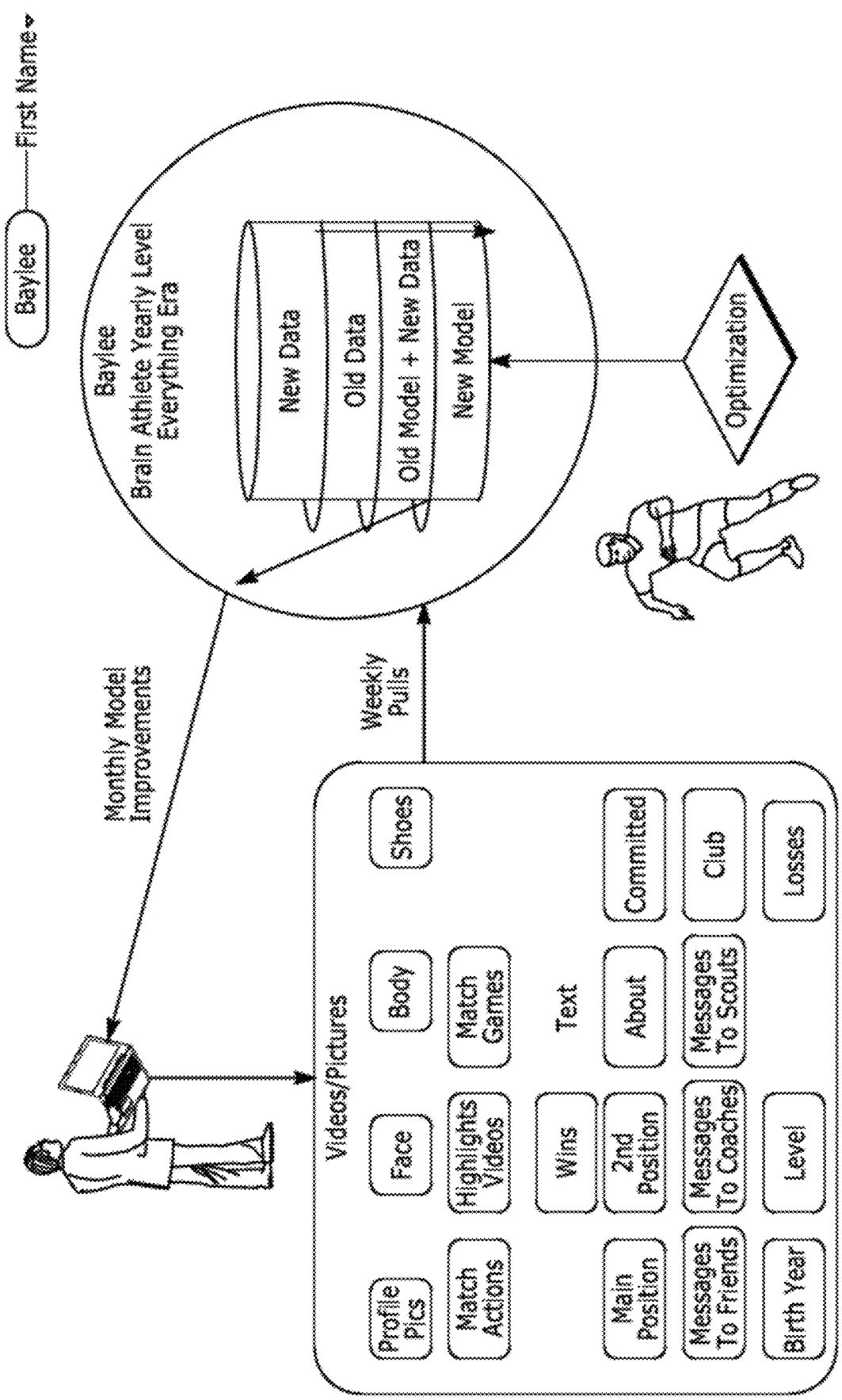
FIG. 11 illustrates an example normalization model.

In particular embodiments, the wearable device 201 may be a wearable buckle, illustrated in FIGS. 5A-5C and FIG. 7A or waist band clip, illustrated in FIG. 6 and FIG. 7B provides at least GPS and accelerometer data. In particular embodiments, the wearable device 201 may be embodied as a buckle that is a wearable all in one device which is worn at the waist and has the drawstring fitted through the shorts with a chord clamp to stay affixed to the athlete. In addition, it can be worn on the back via harness and on the shoe or calf via sleeve of the player. The wearable device 201 may recognize the other devices (that a user may be wearing, e.g., a user may have two or more wearable devices 201) and compare data among devices to filter out anomalies and noise to present the best data from all sensors being worn. In addition, the wearable device 201 may have a compartment for a patch and a clip to store these wearable items keeping everything together. The data may be a closed system for the athlete. For a patch embodiment as shown in FIGS. 8A-8C, the wearable device 201 may be worn on the chest near the heart. The materials for the patch embodiment may be generated in a environmentally friendly factory and may be biodegradable. The wearable device 201 may be made specifically for high intensity sports and may be able to detect cortisol stress, heart rate, electrolyte replenishment. The wearable device 201 may also have a voice recorder to measure bioacoustics which when the athlete speaks before and after the match for 20 seconds can analyze the contents in their blood to detect athlete readiness. The wearable device 201 may be embodied as a clip, which may be worn on the waist and detect steps, distance ran, top speed, average speed, accelerations, decelerations, heat map. The wearable device 201 may be embodied as a wearable boot as shown in FIG. 9, where the wearable device 201 may have 7 sensors and is able to detect heart rate, have pressure sensors for striking, have accelerometers for jumping and boot impact, GPS for positioning and average speed top speed, acceleration, deceleration, magnetometer for indoor positioning, gyroscope for direction and lean, and a proximity sensor using a constant wave of pulse or vibration to sense other players around the player. The wearable device 201 may be possible to achieve using Moore's law to bend light and can be placed on the heel of the athlete. The wearable buckle may have one or more of an accelerometer, GPS, a magnetometer, and a gyroscope and can measure top speed, distance ran, average speed, accelerations, decelerations, sprints, power, caloric burn, heat map. The data collected may be more accurate based upon the position in which the wearable device 201 is placed on the body of the athlete. The wearable boot using proximity sensors may provide an automated stat named athlete creativity or athlete IQ, which can show a map and footspeed of a player in tight spaces and how the athlete got out of problems against their peers. This data collected from the wearable device 201 in various embodiments may be automated and compared and benchmarked among their peers. The features are included above as measurements. Players may be shown longitudinal graphs of their data along with who is the top player in their league as the benchmark along with predictions of what the athlete needs to do in order to perform better as well as what their predicted data is the next game and next practice. In addition, the wearable devices 201 may show game leaders, leader boards, what happened last practice so players may consistently gauge their development along with the coaches and the scouts. Lastly, this data will be aggregated with nutritional and sleep data in order to provide a holistic comprehensive blueprint of the player and whether they are on track to meet goals or not on track as well as overall health. For example a player performing at a high level without sleep and nutrition may be at risk. Players, parents, coaches, and peers may have access to this information (based on permissions given out by the player) and can play a pivotal role in a person's life. The wearable device 201 may have the following features:

Contextual analysis
Ball detection
Goal detection
Remote tracking
Player performance metrics (e.g., speed, distance, top speed, injury prevention, power, fitness progression, recovery time, number of changes of direction, number of sprints, explosive index, etc.)
Acceleration of player development
Live data streaming
Player ratings and position comparisons
Holistic normalization model: This normalization model considers the video event data in addition to wearable biomechanical and other pieces of data in order to objectively rank a player effectively. The normalization model as shown in FIG. 11 may maintain a player chart for a player. The player chart may include one or more of a first name, last name, birth year, graduation year, foot, location data, club, club logo, favorite club, game data (e.g., videos of games, statistics, and the like), publish reel, followers (on social media), comments off of video, preferred boot, technical metrics, physiological metrics, sleep, nutrition, ranking, % changes, and other player characteristics.
AI/ML to determine what skill(s) needs development. Through utilizing models and strategic benchmarking the top athletes positionally and further using subject matter experts to calibrate these stats, the system can build in intelligence with machine learning of the top players in the world within target ages (e.g., for comparing junior competitors, for comparing rookies, for comparing professionals) and more in order to derive positional benchmarks to identify what the top level players can do. Further, the system can use these models to gauge player performance automatically. The system can further show players who compare similar in skill and also predict which environments which would be best suited for the athlete. The AI/ML can self-correct based on inputs by the player, coach, and scout. The system may learn what a certain player looks like based on the data provided by the users, video input, meta data, and text natural language processing. The system may track that player, and auto tag actions itself based on the more data it obtains. The system may become more accurate in making its own specific and individualized decisions about development, predictions, valuations, rankings, etc. Data may be stored weekly for each user in his/her critical section of the operational data repository. Learning algorithms may cause the operating system to become more accurate until minimal human intervention is required. True auto personalized coaching can take over and lend a serious hand in player's development.
Biometrics via heart rate, the implementation of heart rate sensing can be achieved in by smart clothing which is developed specifically for the soccer player to have a tight fit in the heart/chest area but not too restrictive so comfort doesn't compromise the player in any way.
Predictive analysis, what value a player may be able to achieve in the next game. Based on previous game analysis and an understanding of the competitor may be able to automatically predict each performance metric which an athlete should be able to achieve. This may greatly assist as inspiration to the athlete to beat their predicted statistics.

In particular embodiments, a wearable boot embodiment, illustrated in FIG. 9, provides multiple sensory units (e.g., GPS, accelerometer, pressure sensors, proximity sensors, haptics, moisture, individual goal planning LED feedback, and heart rate, etc.). In particular embodiments, the proximity sensor may be configured to detect who is around the player on the map. For training there may be a haptic sensor which can let a player know where other players or people are. This can be useful for military or defense operations down the road. As an example and not by way of limitation, the wearable device 201 may sense danger, such as if there are people nearby, a detected bomb, etc. The proximity sensor may send a pulse, such as waves built into the heel of a wearable boot around the player like cellular and can detect movement, devices connected to internet, certain chemicals, or items which could be hidden. The functionality may be similar to sonar or airport x-ray technology. Through accurate, low-latency data acquisition coaches and players can make informed "game-time" decisions and adjustments. The system can have the following features:

Detection of proximity of surrounding players
Contextual analysis
Ball detection
Goal detection
Duel detection
Kick analysis
Remote tracking
Player performance metrics (e.g., speed, distance, pass completions, goals, assists, duel efficiency, runs, etc.)
Accelerates player development
Live data streaming
Player ratings and position comparisons
Biometrics via heart rate
Predictive analysis of what the player may achieve in the next game. Based on previous game analysis and an understanding of the competitor may be able to automatically predict each performance metric which an athlete should be able to achieve. This may greatly assist as inspiration to the athlete to beat their predicted statistics.

Figure 10:
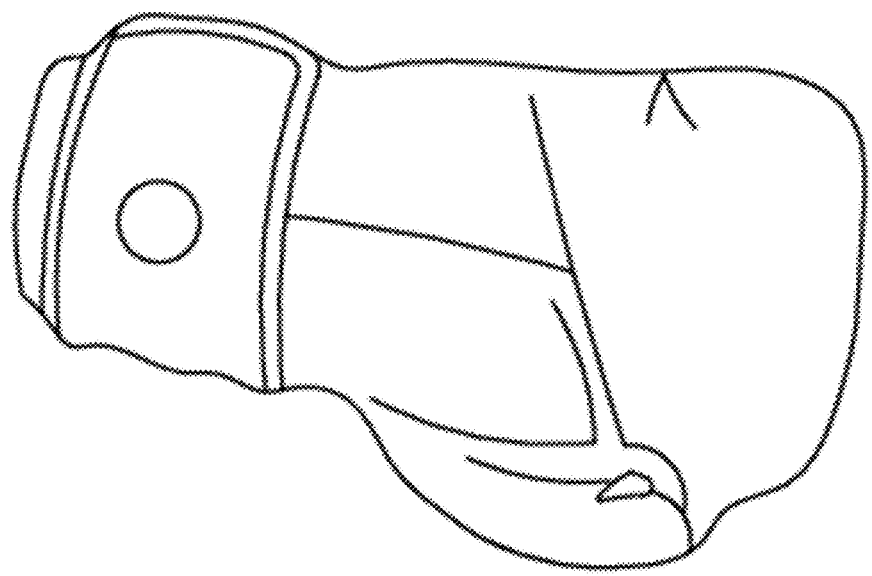
FIG. 10 illustrates an example embodiment of a boxing glove style sensor.
Figure 10:
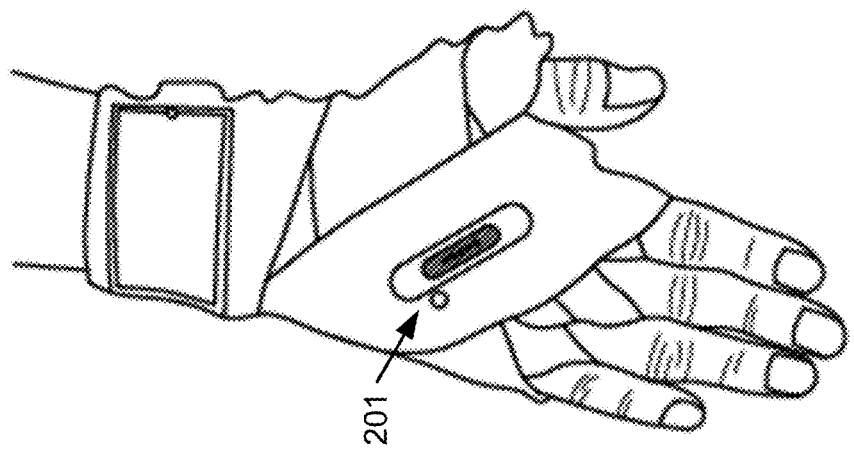
Figure 10:
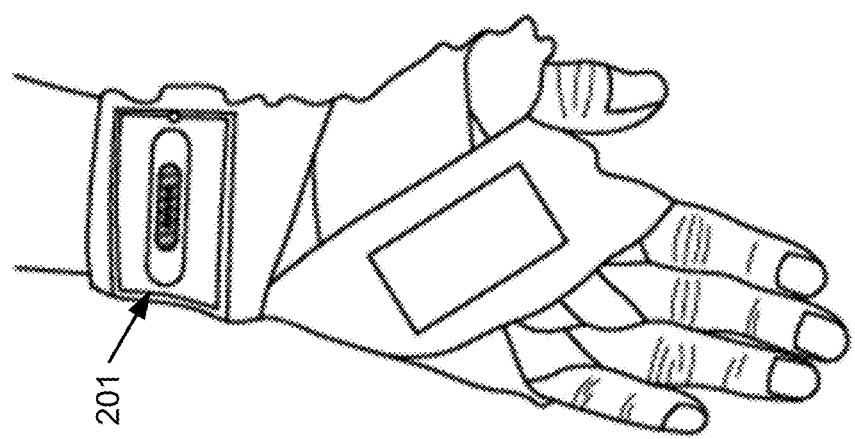

FIG. 10 illustrates an example embodiment of a boxing glove style wearable device 201.

In particular embodiments, the Sports Operating System may use bioacoustics to measure chemicals in the body which may provide insight into the readiness of the athlete. For instance, how much lactic acid is in the blood before the start of a match, how much electrolytes are in the blood, and other chemicals which are produced when under stress, in pain/injury, and an illness. This may keep players more healthy, safe, and also provide an edge for performance.

Analytics computing normalization allows for computer vision and biomechanical data to be tracked aggregated and through the use of position specific contextual analysis not only allows for accurate and reliable player rankings but also provides future predictive player performance data modeling and rankings. Health data may become integrated and through natural language processing (NLP) or natural language understanding (NLU) may better understand behaviors to provide insight into their performance, health, ID injury risk, and predict performance comparison against peers. The Sports Operating System can be optimized with several real-time algorithms providing a "sports center" which will be ever changing as players improve and more player data is analyzed. Based on all of the data provided within a player profile an opportunity to evaluate a player will also be important.

In particular embodiments, this system may also provide a social experience for those monitored (e.g., sports athletes, dancers, musicians). The system may detect how many fans or followers they have and provide opportunities for individuals to provide messages to athletes allowing for a stronger connection and better understanding of organizations.

Particular embodiments of the system disclosed herein, as an integrated solution, may provide one or more of the results, effects, or technical benefits discussed herein. Currently there is very little context in the market to help an athlete best understand themselves, make adjustments based on their behavior, and compare themselves to their competition. Further what is most important is for them to be able to improve based on expert subject matter and data science normalization techniques. Since there is little data tracked within amateur players benchmarks and professional guidance backed by data is nascent. Coaches rely on the naked eye to decide a player's performance level and the amount of progress being made over time. This makes a coach's job very labor intensive and renders them to be less time effective.

The video component processes data via computer vision and automatically propagates events synchronized with wearable data. This uniquely tracks individual players and processes the information contextually. Additionally, the ability to automatically clip player performance based on specific defined soccer actions does not exist, instead it must be performed by hand. In restricted conditions, machines can automatically film players but have not been able to automatically clip and store each clip event data for review later (e.g., by the player, coach, scout, etc.).

The smaller form factor of the belt buckle and clip wearable reduces expenditures for components, manufacturing, assembly and test. This also reduces bulkiness, increasing wearer comfort to improve compliance and consistency of wearing. Continuous-time sensor interface mitigates bandwidth, linearity, power consumption and noise trade-offs inherent in its discrete-time counterpart thereby achieving accuracy more efficiently. Low data latency enables real-time adjustments resulting in better decisions and enhanced player performance. Wearable is not player-obstructive. Stride detection and baseline of the player provides a more precise and accurate measurement detecting accelerations, velocity, and speed. This new method is a more individualized and accurate method specific to the player. With a wearable form factor shaped for the waist and placed in a player's center of gravity it allows for more accurate collection of event data metric data collection and measurement. In addition, as this is designed for the draw string the wearable can be placed on the shoes collecting additional data measurements outside of just acceleration and GPS based data. In addition to this form factor, in particular embodiments a patch embodiment, illustrated in FIGS. 8A-8C, can be used in combination with multiple small drones enables the ability to harvest performance data in-real-time having access to a fan-experience like never before. In particular embodiments, multiple drones may coordinate together to best capture an athletic event (e.g., a game, practice, etc.). The group of drones may communicate with a system (e.g., the Sports Operating System) to determine where to capture images of an athletic event. As an example and not by way of limitation, the group of drone may send data, such as optical sensor data of cameras coupled to the drones to the Sports Operating System, which would perform image analysis and apply a machine-learning algorithm to the output of the image analysis and received sensor data from wearable devices of the players to determine what to capture in an athletic event. As an example and not by way of limitation, for a soccer match, the focus of the athletic event may be on the player who currently has the ball. The Sports Operating System may receive images from multiple drones to identify the position, trajectory, etc. of the ball and determine (using an ML algorithm) where the group of drones should be distributed over a field to accurately capture the athletic event. Multiple factors may be considered by the ML algorithm, such as environment of the athletic event, weather, time of day, how many drones are being deployed, battery life of drones, specific elements of the athletic event (e.g., sand in golf, yardage lines in football, and the like), and other factors particular to the context of the athletic event. The ML algorithm may be trained on data from sports broadcasts, where the optimal viewing angles are determined based on previous sports broadcasts. The Sports Operating System may identify special attributes of players and may deploy the group of drones based on these special attributes. As an example and not by way of limitation, if a player has a unique characteristic for an athletic category, such as a certain celebration, then the group of drones may be deployed to capture the player performing the certain celebration. As another example and not by way of limitation, if a player is identified by the Sports Operating System as having a very high-speed characteristic, then the Sports Operating System may deploy the group of drones to capture the particular player using their speed during an athletic event. As an example and not by way of limitation, when the Sports Operating System detects the player reaching 95% of their max speed and has a ball (in soccer), then the Sports Operating System may deploy the group of drones to capture video of the player.

Comfort for players using wearable technology is crucial as the players who are interested in obtaining an advantage are also not interested in feeling uncomfortable during play. This annoyance becomes a huge disadvantage to the athlete because the wearable tech irritates a player, or even as research suggests, due to untethered placement pushes a player to use compensatory movement patterns which possibly puts the athlete at an increased risk for injury. Currently companies are employing either sports bras to hold large puck like sensors, ill-fitting bands that fit around a player's torso to collect heart rate and respiration information, sensors on the boot which could create an unnatural touch, or even wearable sleeves tightly compressed around the player's calf which can dig into the muscle. However, all of these are examples of products that are noticeable to the player and can have an uncomfortable/negative impact on a player's performance. At this time there is no product on the market which is unnoticeable to the player, highly accurate, and feeds into a greater system which normalizes data dynamically every time an athlete plays a match to compare against other athletes in addition to allowing athletes to be social connecting with friends anywhere any place, and allowing scouts to find players on a map like feature. There is no product in the market which allows scouts and coaches to see real-time data on the players which using AI/ML techniques has ranked players based on the different types of data expressed above in addition to wearable biometric data.

In particular embodiments, the Sports Operating System may additionally use a combination of drone technology with AI along with cameras with AI models paired with augmented reality to provide a coach with a real-time stream of the game and even be able to call game time decisions as if they are there. Coaches at an alternate site away from the field use a glasses augmented reality (AR) system or microphone and are able to communicate with their coaching/staff, by visualizing their game in a three dimensional birds-eye view may be able to spot potential exposure opportunities of an opponent and be able to make substitutions completely away from the field. Based on the coach's style of play, which may be predetermined by the system or preprogrammed into the system, the three-dimensional field may highlight an opponent's deficiencies which may be exposed tactically. For example highlighting a certain player who is the weakest or strongest link or highlighting a side of the field at a given time which could be exposed based on a team's current run of play and the opponent's formation and performance. This may help the coach make stronger objective substitutions and give rise to a more impactful half time speech to take advantage of an opponent.

In particular embodiments, the Sports Operating System may also support individual development planning into each of its products which is a differentiation feature compared to the market. Each individual is different with different strengths and goals. The ability to program these goals and have the wearable immediately activate or illuminate with certain LED upon achieving is a huge achievement. As an example and not by way of limitation, built-in AI algorithms may enable players and coaches to have suggested goals based on their previous data and predicted outcomes. Five LED lights on the wearable can light up upon successfully achieving such goals. Coaches and scouts may be able to securely log-in and set goals for an athlete based on individual needs. This may provide challenges for the athlete to promote increased performance. Notifications may be sent to the athlete and challenges can be accepted or declined upon receiving the notifications. As an example and not by way of limitation, notifications may be sent via a wireless connection. The wearable device 201 may use cellular antennas to automatically send data and notifications to a phone, store in the cloud, etc. The player may configure a setting on their phone or device to instantly receive the data. The Sports Operating System may track the progress on completing these goals and provide the progress in a report sent to the player and other users that have permission to access the report (e.g., coaches and scouts).

Since subject matter experts have seen and experienced the game with a significant trained eye. The specific types of moments which a player can escape a situation or various types of statistics when combined together can distinguish or separate a player from the rest, this information and intelligence is built into the wearable and CV tools and automatically filters and evaluates players. At this time only data is visible. Thus, the system supports being able to notice an injury before it happens or notice the type of injury and the severity exactly when it happens through the CV, AI, and wearable technology. This feature may be particularly valuable for amateur players. The data science process is a very distinct one which starts with a narrow case study around context and ends with a large amount of data using regression and ends with a subject matter expert calibration process to ensure the most precise intelligence is built into the system. As the system obtains more data and learns about the player and the players within the system the system gets smarter and in turn makes predictions based on the data. This is an evolution of sports within the data.

In particular embodiments, the system may include additional features described herein. In particular embodiments, the system may include wi-fi, cloud services, remote tracking mobile application, pitch location, player speed, kick detection, velocity, point of contact analysis, live biomechanics analysis, game IQ assessment, player ratings, player identification, battery charging, low power, ball tracking, goal detection, player tracking subscriptions, contextual analysis, scouting, and individual development plan (IDP).

The system may perform feature comparisons on one or more features of a player to one or more features of other players. The Sports Operating System may constantly compare data of a player to a baseline but also to other players at their level which is fed to a large database, which is constantly recalibrating. The features can include distance, speed, sprints, max efforts, minutes played, player pitch location, kick detection, kick speed, goal conversion, contact analysis, contextual analysis, live data streaming, remote tracking, ball tracking, parent subscriptions, player ratings, player scouting, and IDP.

Particular embodiments disclosed herein may be implemented using one or more example architectures.

Particular embodiments may repeat one or more steps of the example process(es), where appropriate. Although this disclosure describes and illustrates particular steps of the example process(es) as occurring in a particular order, this disclosure contemplates any suitable steps of the example process(es) occurring in any suitable order. Moreover, although this disclosure describes and illustrates an example process, this disclosure contemplates any suitable process including any suitable steps, which may include all, some, or none of the steps of the example process(es), where appropriate. Furthermore, although this disclosure describes and illustrates particular components, devices, or systems carrying out particular steps of the example process(es), this disclosure contemplates any suitable combination of any suitable components, devices, or systems carrying out any suitable steps of the example process(es).

A controller unit (dummy wearable) which is network synced with other units can act as a coaches input to the system. Adding several buttons could allow a coach to queue specific tasks or key points in time in the data. A sensor may be placed on all athletes to provide player communication. A coach can buzz another coach or player to initiate communication without getting in the way of practice. Or a coach can speak to a player while in the middle of a play.

Particular embodiments disclosed herein may be implemented in relation to different example use cases.

Use Case #1: Provide Contextual Information Pertaining to Offensive and Defensive Player Interaction.

Summary: A player on the offensive team possesses the ball. Determine the number of defenders "marking" the player.

Actors: offensive players; defensive players

Preconditions: Internet access; offensive player is in possession of the ball during active play on the pitch Description:
1. Determine location of offensive player on the pitch (e.g., using GPS).
2. Determine location of defenders marking the player (e.g., using proximity sensors).
3. Provide contextual visual display showing offensive players and respective defenders.

The use case terminates at this point.

Use Case #2: Track the Ball Movement Between Multiple Team Players

Summary: The offensive team possesses the ball. Track the movement of the ball between team members.

Actors: offensive players; ball

Preconditions: Internet access; active play on the pitch within a single team possession Description:
1. Determine location of offensive player #1 in possession of the ball (e.g., using GPS, pressure sensor).
2. Determine location of offensive player #2 (e.g., using GPS).
3. Determine offensive player #2 has possession of the ball (e.g., using pressure sensors).
4. Provide a visual display showing displacement of the ball from one player location to another.

The use case terminates at this point.

Use Case #3: Detect and Analyze a Kick

Summary: The offensive team possesses the ball. Determine the point of contact for the kick and the kick velocity using the sensors of the boot and computer vision.

Actors: offensive player; ball

Preconditions: Internet access; active play on the pitch

Description:
1. Detect a player kick and a point of contact (e.g., using pressure sensors).
2. Determine kick velocity (e.g., using pressure sensors).
3. Provide visual display for metrics above.

The use case terminates at this point.

Use Case #4: Detect a Goal

Summary: The offensive team possesses the ball. Determine when a team player scores a goal.

Actors: offensive players; ball

Preconditions: Internet access; active play on the pitch; not initial kickoff and time is remaining in the half Description:
1. Detect a player kick and point of contact (e.g., using pressure sensors).
2. Determine kick velocity (e.g., using pressure sensors).
3. Determine if another team member has received the ball (e.g., using pressure sensors).
4. Determine if team members line up for kickoff (e.g., using GPS).
5. Update and display team score.

The use case terminates at this point.

Use Case #5: Analyze a Duel

Summary: A player on the offensive team possesses the ball. Determine the number of defenders "marking" the player and if the team retains possession.

Actors: offensive players; defensive players

Preconditions: Internet access; offensive player is in possession of the ball during active play on the pitch and no goal is scored Description:
1. Determine location of offensive player on the pitch (e.g., using GPS).
2. Determine location of defenders marking the player (e.g., using proximity sensors).
3. Detect if player retains the ball (e.g., using pressure sensors).
4. Determine if the ball has been kicked (e.g., using pressure sensors).
5. Determine if another team member has received the ball (e.g., using pressure sensors).
6. Determine if team members line up for kickoff (e.g., using GPS).
7. Possession has been lost.

The use case terminates at this point.

Use Case #6: Provide Sensory Feedback to Player

Summary: A player on the offensive team possesses the ball. Determine the number of defenders "marking" the player. If a defender is within a certain range the player receives sensory notification. This may be selectively activated for training purposes.

Actors: offensive players; defensive players

Preconditions: Internet access; offensive player is in possession of the ball during active play on the pitch Description:
1. Determine location of offensive player on the pitch (e.g., using GPS).
2. Determine location of defenders marking the player (e.g., using proximity sensors).
3. Determine if a single defender is within a specified range of the player (e.g., using proximity sensors).
4. Provide sensory notification.

The use case terminates at this point.

Use Case #7: Track Player Remotely as Organization Member

Summary: Monitor player performance remotely via cloud services.

Actors: staff viewer; cloud

Preconditions: Internet access; cloud access privileges

DESCRIPTION

1. Receive access code (e.g., using email or short-message service (SMS)).
2. Use access code and view team performance.
3. As an organization member, send requests and instructions.

The use case terminates at this point.

Use Case #8: Track Player Remotely as Non Player

Summary: Monitor player performance remotely via cloud services.

Actors: viewer; cloud

Preconditions: Internet access; cloud access privileges

Description:
1. Receive access code (e.g., using email or SMS).
2. Use access code and view team performance.
3. As a limited-access player, view metrics pertaining to a specific player only.

The use case terminates at this point.

Use Case #9: Scout players remotely

Summary: A prospective scout can search and view player performance metrics and rating scores per geographic location via metadata AI/ML video.

Actors: video from drone or camera; scout; cloud

Preconditions: Internet access; player profile exists; access privileges provided Description:
1. Video is being recorded live or is being accessed via database.
2. Scout client receives access code (e.g., using email or SMS) notification that a player of specific interest should be scouted and to log in at their leisure either live or not live.
3. These games are viewable on a television or computing device or through AR experiences.
4. Use access code and view player performance.
5. Scout has access to the player metrics and other players around the world which are similar.
6. Scout is satisfied with what they see and ends the session.
7. Scout contacts coach and or player depending on role based access.

The use case terminates at this point.

Use Case #10: Coach Players Remotely Via Augmented Reality

Summary: A coach can view players from her team from a remote location and have a near real-time experience. Couch can also speak to her team as if she is there, hear the crowd, and make decisions (e.g., on substitutions) for her team. On a virtual reality display, the coach can see opportunities to exploit opponent weaknesses based on the type of style of play or spatial algorithms built into models. Remote viewers from around the world may be able to log into the same game and watch.

Actors: coach; cloud

Preconditions: Internet access; player profiles exists; access privileges provided Description:
1. Receive access code (e.g., using email or SMS).
2. Use access code and view event player performance.
3. Speak and observe making substitutions, engage with others who may be invited to access the game via code.
4. Game ends and the main client user terminates the session or assigns a new leader of the session upon game ending.

The use case terminates at this point.

Use Case #11: Individual athletes obtain own video

Summary: Individual athletes obtain their own video data involved within the play. Video data may be graded by degree of difficulty and degree of execution via statistical modelling. The players play within the game and are involved in several plays within the course of a game. These moments may last up to a minute long sometimes. While in these moments the players are performing actions, which are a certain level of difficulty. These are graded on a scale and added at the end of their total chains.

Actors: player; video; cloud; Sports Operating System client; AI computer vision algorithms Preconditions: Internet access; player profiles exist; access privileges provided Description:
1. Retrieve video data from drone or camera device.
2. Log into Sports Operating System with secure login credentials.
3. Upload match data and click on process data.
4. Data is cleaned and arrives via the player of interest.
5. Each moment the player is involved in is rendered and accessible.
6. The moments are judged via AI and players are assessed with a degree of difficulty within that game based on the level of play. Players are also assessed against peers and benchmark algorithms and data.
7. User is satisfied with what they observe, logs out, and the session expires.

The use case terminates at this point.

Use Case #12: Individual Development Planning and AI Predictive Goal Planning.

Summary: The player, who is using the belt buckle or belt clip, or additional Sports Operating System wearables, may have lights or other notifiers which are programmed into the wearable. Each light is programmable based on the player's unique skills, interests, strengths, or deficiencies for added excitement, development, and gamification.

Actors: player; wearable; cloud gateway

Preconditions: Internet access; player profiles exists; access privileges provided Description:
1. Player/coach logs into Sports Operating System client via secure password or SMS.
2. Player/coach reviews data and either selects own goals or selects suggested goals.
3. Player puts on wearable.
4. Coach enables a secure session and inputs credentials.
5. Coach obtains notification and accepts user agreement.
6. Player performs and data is recorded.
7. Programmed goals are met.
8. LED lights are lit based on achievement.
9. Data is recorded.

10. Game ends.
11. Coach hits game complete or the session expires based on lack of use.

The use case terminates at this time.

Use Case #13: Injury Risk Prevention Index:

Summary: Injury risk prevention index is a measurement which is provided to each athlete after training, at the end of the first half if they are using a real-time version of the Sports Operating System, or, if not, at the end of the game. The Sports Operating System measures wear and tear on the player's body. Using a number of measurements, including, but not limited to, those discussed below, the Sports Operating System calculates and illustrates force and stress on the body over a certain amount of time based on, e.g., velocity and distance. The total amount of this energy and power is measured and presented to the player. The Sports Operating System collects acceleration and, based on the known weight (e.g., mass) and velocity of the player, derives force. In addition, also the amount of work an athlete does which is force multiplied by distance. Therefore, the Sports Operating System can determine the amount of power an athlete is putting on their body (e.g., force on joints) and the future potential amount of power an athlete is exerting. Through the Sports Operating System, CV and AI are able to identify harmful workloads and trigger warning signs to the athlete and the coach or trainer to protect the player. This can provide enhanced injury prevention protocols for athletes and provide a safer and healthier career. An algorithm is used based on, e.g., the factors below in order to provide a score and based on research and subject matter expertise given the amount of load or stress on an athlete. A reference value is provided for this score and updated within a time series database.

power=work/time=(watt or joules)/sec

In sports, power=work/velocity power=energy/time=force×distance/time=force×velocity force=mass×acceleration velocity=initial velocity+(acceleration×time)

velocity=distance/time potential energy=mass×gravity×height work=force×distance force=mass×acceleration Actors: player; cloud Preconditions: Internet access; player profiles exist; access privileges provided Description:
1. Receive access code (e.g., using email or SMS).
2. Use access code and view event player performance.
3. Prior to the game the athlete sees their injury risk prevention score and begins to play
4. Athlete completes three quarters of the game and receives a notification (e.g., through a haptic buzz) indicating that they are at risk of an injury. The coach is also sent a notification to a computing device (e.g., mobile device, laptop, etc.). The coach may also hear a loud noise that alerts them their play may be at risk for injury.
5. Coach decides to allow player to play.
6. Player receives injury and the event is logged and stored for use in future research.
7. Information about the injury is entered at the time of the injury via the athlete and coach.
8. The athlete logs out of the wearable device or CV.
9. Game ends and the main client user terminates the session.

The use case terminates at this point.

Use Case #14: Smart Position

Summary: Smart Position enables the ability to collect data and score the performance of the athlete only when they are playing in the role intended by the coach. The CV and wearable can detect when a player has moved to another position or, the coach has intentionally moved the player to another position in the middle of the game (e.g., during a substitution), including without human intervention. By doing this, and combining AI with the Sports Operating System, contextual position specific performance evaluation algorithms the system can predict/suggest which position is best suited for the player overall and within the given team based on the abilities of the players around the specific player. As the system collects and gathers more information, the system also becomes more intelligent. Thus, this prediction can change to a different position. Also, the player may change from time to time and may play on new teams and in new roles. Thus, the system can adapt as player data changes and make predictions on this new data in order to achieve the best result possible.

Actors: player; cloud

Preconditions: Internet access; CV; wearable; access privileges provided

Description:
1. Player begins performance.
2. Player changes position halfway through the first half.
3. Player changes to a new position.
4. Coach subs player out.
5. Player changes to a new third position.
6. Player is scored at each of the three positions during their time playing in the positions. Algorithm accounts for the variation when contextually evaluating the player based on data science and human calibration.
7. Data is collected, and the most appropriate position is suggested, however, all three positions have data stored for later aggregation.
8. The game ends and the user logs out.

The use case terminates at this point.

Use Case #15: Sports Operating System Augmented Reality (AR)

Summary: The Sports Operating System AR enables injured players, additional staff, and also full-time/head coaches to view the game after playing leveraging CV and AR in a new three-dimensional (3D) perspective with metrics while the game is going on. This assists in developing a whole new perspective. Contextual information is provided to viewers while watching each play as each play evolves making for a more powerful engrossing experience and enhanced learning opportunity.

Actors: player; cloud

Preconditions: Internet access; video and CV; Sports Operating System SportsVision; access privileges provided Description:
1. Login to ARVision App and receive access code (e.g., using email or SMS).
2. Use access code.
3. Use SportsVision glasses.
4. View game information.

5. Communicate with friends, who may be logged in watching the game as well, via voice through the glasses.
6. The game ends and the user logs out.

The use case terminates at this point.

Use Case #16: Sports Operating System CV Automated Highlight Aggregation.

Summary: The athlete compiles a library of highlights from the computer vision system. The CV system of Sports Operating System is automatically adding to the library as player plays. The player can also upload highlights they choose to store in their library on their own. If they choose to, based on their position and choice of minutes can select "automate highlight" and a highlight tape of a few minutes with the most salient points within their position may be rendered. This can, for example, save the player time and labor clipping highlight tapes. If the athlete chooses to select the auto feature, these highlight tapes may be automatically run periodically upon the choice of the athlete.

Actors: user; cloud
Preconditions: Internet access; profile
Description:
1. User enters Sports Operating System login/registration.
2. User navigates to highlight section of the profile.
3. User selects automate highlight.
4. Highlight automatically renders.
5. Athlete changes their selection to automatically rendering highlight every month.
6. Athlete logs off.
7. Session terminates.

The use case terminates at this point.

Use Case #17: Sports Operating System TrueValu Algorithm

Summary: The Sports Operating System TrueValu algorithm considers contextual athlete data and the data science methodology which assists in measuring and rendering a value of each statistic and the athlete's contribution. In addition, before a game, each player is scored using the Sports Operating System TruValu algorithm and can determine who is valued more and obtain a more precise odds or prediction for who is favored and how significantly. The user can also watch games in the Sports Operating System application and watch using the AR technology as well to obtain a more engrossing experience.

Actors: user; cloud
Preconditions: Internet access; profile
Description:
1. User logs into Sports Operating System and reviews "game" environment.
2. Game environment enables a fan to register and review their favorite players in a whole new light obtaining data on them and able to make decisions on betting, etc.
3. User reviews a particular game which is upcoming and reviews Sports Operating System TruValu for each player.
4. User also reviews favorite to win and by what percentage.
5. User can watch the game on-line and participate in side activities using Sports Operating System AR.
6. Game completes.
7. User logs off.
8. Session terminates.

The use case terminates at this point.

Use Case #18: Sports Operating System Sports Vision AR Glasses

Summary: This hardware is built for fans to wear and utilize on the sidelines and is processed in-app real-time with the computer vision in order to obtain a 3D AR or mixed reality (MR) enhanced environment. The user can also access each of the players' stats, such as who are the leaders of the game in particular categories and who are the leaders compared to players outside of the game, within the league, or around the world, within a given position, or age group.

Actors: player; fan; glasses; CV; wearable; cloud
Preconditions: Internet access; CV; AR; SportsVision; access privileges provided
Description:
1. Player has a profile on the Sports Operating System.
2. Fan logs in within app and uses Sports Operating System SportsVision glasses via internet connection.
3. Fan uses an access code for secure session.
4. Sports Operating System SportsVision session begins.
5. View player in 3D within a virtual environment by choice of the fan.
6. Fan sees the player and metrics as well as additional players from around the world. Fan can also see alternate games.
7. Fan can communicate with other fans on the team or fans around the world based on a particular game.
8. The game ends and the user logs out.

The use case terminates at this point.

Use Case #19: Sports Operating System MR DreamV

Summary: This hardware is built for players to wear who can then can play against other players around the world within a mixed reality environment. The athlete who trains achieves and acquires skill. Based on that level of skill, the user creates a virtual presence (e.g., an avatar) which they can play with players from around the world at the level of skill they have achieved. Players can recruit each other. This is all done through Sports Operating System MR DreamV.

Actors: player; glasses; cloud
Preconditions: Internet access; DreamV glasses; access privileges provided
Description:
1. Player has a profile on the Sports Operating System.
2. Player logs in within app and uses the glasses via internet connection.
3. Player finds a virtual game to participate in and play.
4. Users present an access code for secure session based on their level in which they have achieved.
5. Session begins.
6. View and interact with a player in 3D within a mixed virtual environment.
7. The game ends and the user logs out.

The use case terminates at this point.

Use Case #20: Owner/Club Representative Purchases Player Rights Contract Summary Summary: The owner or club representative runs AI algorithms to find a player who would fit well for their club based on, e.g., their own players, style of play, and pre-defined metadata needs. The owner can recruit the player and, where needed, purchase transfer rights via a secure bank portal. The club can exercise the rights assigned within the contract of both parties using, in some embodiments, a blockchain-enabled secure transaction.

Actors: owner/club representative; Sports Operating System; Sports Operating System exchange
Preconditions: Internet access; player profiles exists; access privileges provided; player rights of purchase contract
Description:
1. Owner/club representative logs in via secure password and or SMS notification.

2. Input interests and review market opportunities.
3. Select the opportunity that best matches player needs.
4. Owner executes contract on the client side.
5. Player/agent is notified.
6. Player/agent logs into Sports Operating System securely.
7. Player agent reviews terms of contract and agrees to terms and digitally accepts or denies contract term agreement.
8. Bank exchanges information and pays player agreed terms if contract is accepted.
9. Both parties log out.

The use case terminates at this point.

Use Case #21: Soccer Boot/Cleat (Software & Hardware) Material Unit

Summary: Player wears soccer shoe which includes hardware with built-in sensors, such as those described herein, interfacing with drone technology and providing real-time data to coaches and fans. The sensors can include, for example, a proximity sensor (which may sit at the top of the shoe area giving ability to detect defenders, ball, and goals), moisture sensor (e.g., to detect how damp the surface is which as a variable may drive the behavior of the user to play a certain way), GPS (e.g., to detect where the player is on the pitch), pressure sensor modules (which may sit, e.g., on top of the shoe (e.g., outside, inside, and on the laces or central area of the boot), haptics (e.g., to provide automatic feedback (e.g., vibrate, or play a tune) to the user in a training setting)). In addition, the boot can be made ultra light-weight fiber to offset any additional weight from sensors.

Actors: player; drone; fan; coach; cloud
Preconditions: Internet access; player profile exists; access privileges provided
Description:
1. Receive access code (e.g., using email or SMS).
2. Use access code and view player performance.
3. Player performs using the hardware device which is streaming some lightweight data to the fan and coach.
4. All data which is interacting with the drone technology is being sent to the cloud where data is aggregated with AI/ML and displayed within the user profile. This data can be accessed in near real-time by fans to be able to see how a particular player is performing relative to players from all over the world, for example, within a particular age group and position.
5. In addition, to provide overall performance rankings of how well the player's performance is overall, how well the player's performance was that day against all others in the world, and additional insights. The player can use this information to determine how to progress in their skills become better based on the data being provided. This information may be provided in an auto-coaching manner based upon reviewing thousands of minutes of games to detect the areas a player is performing well and areas of improvement.

The use case terminates at this point.

Use Case #22: Sports Operating System SportsVision AR Glasses Coach View

Summary: This hardware is built for coach to wear and drop into the athlete landscape on a 3D plane to see what the athlete sees and is processed in-app real-time with the computer vision in order to obtain a 3D AR or mixed reality (MR) enhanced environment. The coach and or player engages in the most impactful way by seeing what took place at that time and what options were available. Using automated logic can first make a decision and then by the push of a button can see the preferred decision. Players and coaches can log in with more than one player and relive games and alter decisions to increase learning saving time and money by reducing training sessions which might be avoided by such technology. The user can also click on the player zooming into their decisions and see what happened at different times of the game along with reviewing their aggregated data to drive additional context in decision making. This can be done post processing as well as in real-time with users seeing what decisions are being made and quickly diagnosing good vs bad decisions.

Actors: coach, player, parent, scout, fan, computer vision, computer vision synchronized with wearable device signature, cloud.
Preconditions: Internet access; CV; AR; SportsVision; access privileges provided.
Description:
1. Player has a profile on the Sports Operating System.
2. Coach, player, or other user logs in within app and uses Sports Operating System SportsVision glasses via internet connection.
3. Coach, player, or other user uses an access code for secure session.
4. Sports Operating System SportsVision session begins.
5. View player in 3D within a virtual environment by choice of the user.
6. User sees the player and metrics as well as additional players from around the world. Fan can also see alternate games.
7. User ends session (whether in real-time or a review of the game) and the user logs out. The use case terminates at this point.

Foundational Technologies

Underlying foundational concepts and terms of art relied upon may relate to one or more of the following in particular embodiments:

Internet of Things (IoT);
sensor technology;
embedded systems;
coding algorithms;
mobile applications development;
cloud computing;
moisture/climate sensor: detects the climate e.g. precipitation level degree of rain or dry climate to contextualize play as a rankable factor built into ranking/valuation algorithm;
pH sensor;
chemical sensor: detects hormones of the wearer;
haptic feedback;
triggers/notification;
AI/ML;
exchange of purchasing services and goods;
automated highlight reels;
automated clipping;
social media;
computer vision;
machine learning;
convolution neural networks;
predictive modeling;
drones;
multiple drone visualization;
longitudinal graphical analytics and insights;
data intelligence visualization;
augmented reality.

In all example embodiments described herein, appropriate options, features, and system components may be provided to enable collection, storing, transmission, information security measures (e.g., encryption, authentication/authorization mechanisms), anonymization, pseudonymization, isolation, and aggregation of information in compliance with applicable laws, regulations, and rules. In all example embodiments described herein, appropriate options, features, and system components may be provided to enable protection of privacy for a specific individual, including by way of example and not limitation, generating a report regarding what personal information is being or has been collected and how it is being or may be used, enabling deletion or erasure of any personal information collected, and/or enabling control over the purpose for which any personal information collected is used.

Figure 12:
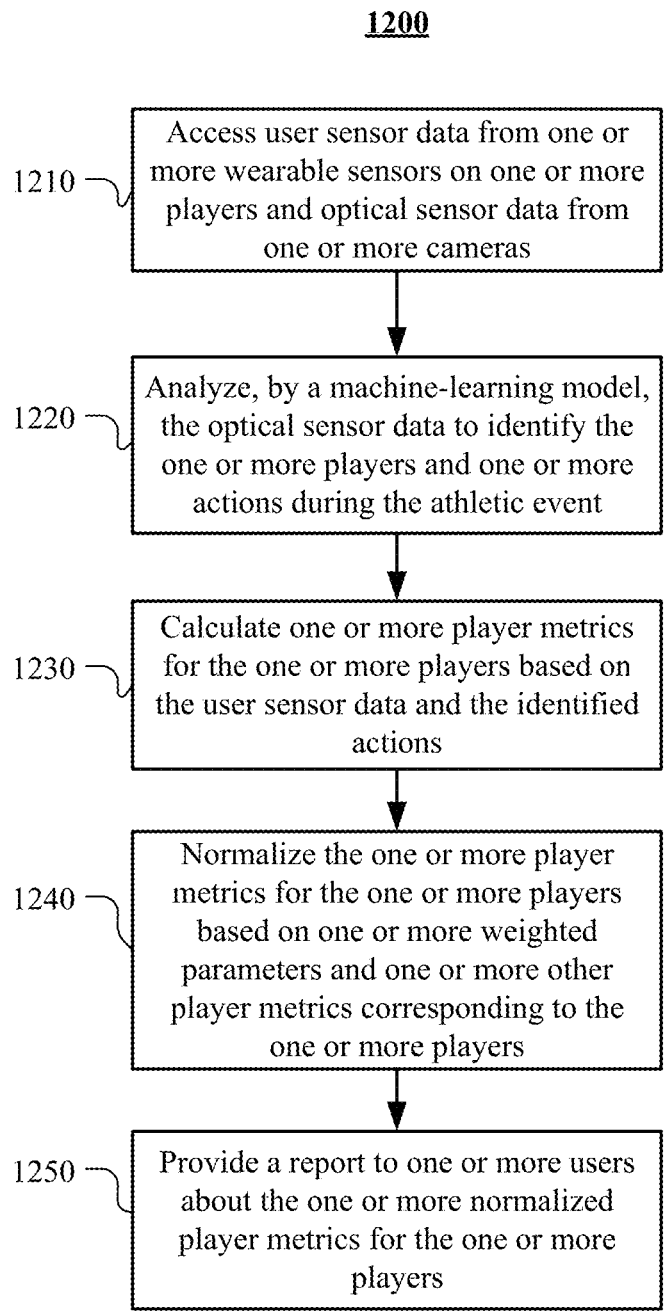
FIG. 12 illustrates an example method for providing a report of normalized player metrics.

FIG. 12 illustrates an example method 1200 for providing a report of normalized player metrics. The method may begin at step 1210, where one or more computing systems may access user sensor data from one or more wearable sensors on one or more players and optical sensor data from one or more cameras. In particular embodiments, the user sensor data may comprise location data of the player and acceleration data. In particular embodiments, the optical sensor data may comprise a plurality of frames portraying the one or more players and a plurality of scenes from an athletic event. At step 1220, the one or more computing systems may analyze, by a machine-learning model, the optical sensor data to identify the one or more players and one or more actions during the athletic event. At step 1230, the one or more computing systems may calculate one or more player metrics for one or more players based on the user sensor data and the identified actions. At step 1240, the one or more computing systems may normalize the one or more player metrics for the one or more players based on one or more weighted parameters and one or more other player metrics corresponding to the one or more players. At step 1250, the one or more computing systems may provide a report to one or more users about the one or more normalized player metrics for the one or more players. Particular embodiments may repeat one or more steps of the method of FIG. 12, where appropriate. Although this disclosure describes and illustrates particular steps of the method of FIG. 12 as occurring in a particular order, this disclosure contemplates any suitable steps of the method of FIG. 12 occurring in any suitable order. Moreover, although this disclosure describes and illustrates an example method for providing a report of normalized player metrics, including the particular steps of the method of FIG. 12, this disclosure contemplates any suitable method of providing a report of normalized player metrics, including any suitable steps, which may include all, some, or none of the steps of the method of FIG. 12, where appropriate. Furthermore, although this disclosure describes and illustrates particular components, devices, or systems carrying out particular steps of the method of FIG. 12, this disclosure contemplates any suitable combination of any suitable components, devices, or systems carrying out any suitable steps of the method of FIG. 12.

Figure 13:
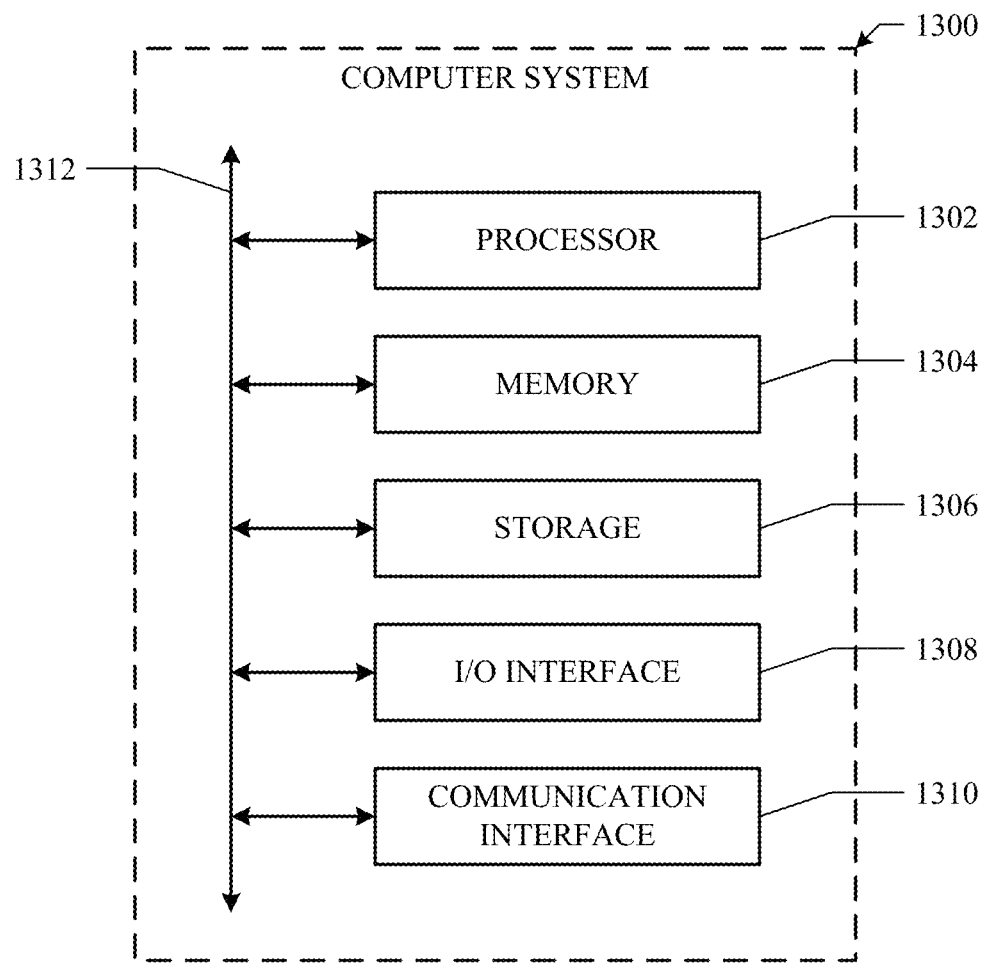
FIG. 13 illustrates an example computer system.

FIG. 13 illustrates an example computer system 1300. In particular embodiments, one or more computer systems 1300 perform one or more steps of one or more methods described or illustrated herein. In particular embodiments, one or more computer systems 1300 provide functionality described or illustrated herein. In particular embodiments, software running on one or more computer systems 1300 performs one or more steps of one or more methods described or illustrated herein or provides functionality described or illustrated herein. Particular embodiments include one or more portions of one or more computer systems 1300. Herein, reference to a computer system may encompass a computing device, and vice versa, where appropriate. Moreover, reference to a computer system may encompass one or more computer systems, where appropriate.

This disclosure contemplates any suitable number of computer systems 1300. This disclosure contemplates computer system 1300 taking any suitable physical form. As example and not by way of limitation, computer system 1300 may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, a personal digital assistant (PDA), a server, a tablet computer system, or a combination of two or more of these. Where appropriate, computer system 1300 may include one or more computer systems 1300; be unitary or distributed; span multiple locations; span multiple machines; span multiple data centers; or reside in a cloud, which may include one or more cloud components in one or more networks. Where appropriate, one or more computer systems 1300 may perform without substantial spatial or temporal limitation one or more steps of one or more methods described or illustrated herein. As an example and not by way of limitation, one or more computer systems 1300 may perform in real time or in batch mode one or more steps of one or more methods described or illustrated herein. One or more computer systems 1300 may perform at different times or at different locations one or more steps of one or more methods described or illustrated herein, where appropriate.

In particular embodiments, computer system 1300 includes a processor 1302, memory 1304, storage 1306, an input/output (I/O) interface 1308, a communication interface 1310, and a bus 1312. Although this disclosure describes and illustrates a particular computer system having a particular number of particular components in a particular arrangement, this disclosure contemplates any suitable computer system having any suitable number of any suitable components in any suitable arrangement.

In particular embodiments, processor 1302 includes hardware for executing instructions, such as those making up a computer program. As an example and not by way of limitation, to execute instructions, processor 1302 may retrieve (or fetch) the instructions from an internal register, an internal cache, memory 1304, or storage 1306; decode and execute them; and then write one or more results to an internal register, an internal cache, memory 1304, or storage 1306. In particular embodiments, processor 1302 may include one or more internal caches for data, instructions, or addresses. This disclosure contemplates processor 1302 including any suitable number of any suitable internal caches, where appropriate. As an example and not by way of limitation, processor 1302 may include one or more instruction caches, one or more data caches, and one or more translation lookaside buffers (TLBs). Instructions in the instruction caches may be copies of instructions in memory 1304 or storage 1306, and the instruction caches may speed up retrieval of those instructions by processor 1302. Data in the data caches may be copies of data in memory 1304 or storage 1306 for instructions executing at processor 1302 to operate on; the results of previous instructions executed at processor 1302 for access by subsequent instructions executing at processor 1302 or for writing to memory 1304 or storage 1306; or other suitable data. The data caches may speed up read or write operations by processor 1302. The TLBs may speed up virtual-address translation for processor 1302. In particular embodiments, processor 1302 may include one or more internal registers for data, instructions, or addresses. This disclosure contemplates processor 1302 including any suitable number of any suitable internal registers, where appropriate. Where appropriate, processor 1302 may include one or more arithmetic logic units (ALUs); be a multi-core processor; or include one or more processors 1302. Although this disclosure describes and illustrates a particular processor, this disclosure contemplates any suitable processor.

In particular embodiments, memory 1304 includes main memory for storing instructions for processor 1302 to execute or data for processor 1302 to operate on. As an example and not by way of limitation, computer system 1300 may load instructions from storage 1306 or another source (such as, for example, another computer system 1300) to memory 1304. Processor 1302 may then load the instructions from memory 1304 to an internal register or internal cache. To execute the instructions, processor 1302 may retrieve the instructions from the internal register or internal cache and decode them. During or after execution of the instructions, processor 1302 may write one or more results (which may be intermediate or final results) to the internal register or internal cache. Processor 1302 may then write one or more of those results to memory 1304. In particular embodiments, processor 1302 executes only instructions in one or more internal registers or internal caches or in memory 1304 (as opposed to storage 1306 or elsewhere) and operates only on data in one or more internal registers or internal caches or in memory 1304 (as opposed to storage 1306 or elsewhere). One or more memory buses (which may each include an address bus and a data bus) may couple processor 1302 to memory 1304. Bus 1312 may include one or more memory buses, as described below. In particular embodiments, one or more memory management units (MMUs) reside between processor 1302 and memory 1304 and facilitate accesses to memory 1304 requested by processor 1302. In particular embodiments, memory 1304 includes random access memory (RAM). This RAM may be volatile memory, where appropriate Where appropriate, this RAM may be dynamic RAM (DRAM) or static RAM (SRAM). Moreover, where appropriate, this RAM may be single-ported or multi-ported RAM. This disclosure contemplates any suitable RAM. Memory 1304 may include one or more memories 1304, where appropriate. Although this disclosure describes and illustrates particular memory, this disclosure contemplates any suitable memory.

In particular embodiments, storage 1306 includes mass storage for data or instructions. As an example and not by way of limitation, storage 1306 may include a hard disk drive (HDD), a floppy disk drive, flash memory, an optical disc, a magneto-optical disc, magnetic tape, or a Universal Serial Bus (USB) drive or a combination of two or more of these. Storage 1306 may include removable or non-removable (or fixed) media, where appropriate. Storage 1306 may be internal or external to computer system 1300, where appropriate. In particular embodiments, storage 1306 is non-volatile, solid-state memory. In particular embodiments, storage 1306 includes read-only memory (ROM). Where appropriate, this ROM may be mask-programmed ROM, programmable ROM (PROM), erasable PROM (EPROM), electrically erasable PROM (EEPROM), electrically alterable ROM (EAROM), or flash memory or a combination of two or more of these. This disclosure contemplates mass storage 1306 taking any suitable physical form. Storage 1306 may include one or more storage control units facilitating communication between processor 1302 and storage 1306, where appropriate. Where appropriate, storage 1306 may include one or more storages 1306. Although this disclosure describes and illustrates particular storage, this disclosure contemplates any suitable storage.

In particular embodiments, I/O interface 1308 includes hardware, software, or both, providing one or more interfaces for communication between computer system 1300 and one or more I/O devices. Computer system 1300 may include one or more of these I/O devices, where appropriate. One or more of these I/O devices may enable communication between a person and computer system 1300. As an example and not by way of limitation, an I/O device may include a keyboard, keypad, microphone, monitor, mouse, printer, scanner, speaker, still camera, stylus, tablet, touch screen, trackball, video camera, another suitable I/O device or a combination of two or more of these. An I/O device may include one or more sensors. This disclosure contemplates any suitable I/O devices and any suitable I/O interfaces 1308 for them. Where appropriate, I/O interface 1308 may include one or more device or software drivers enabling processor 1302 to drive one or more of these I/O devices. I/O interface 1308 may include one or more I/O interfaces 1308, where appropriate. Although this disclosure describes and illustrates a particular I/O interface, this disclosure contemplates any suitable I/O interface.

In particular embodiments, communication interface 1310 includes hardware, software, or both providing one or more interfaces for communication (such as, for example, packet-based communication) between computer system 1300 and one or more other computer systems 1300 or one or more networks. As an example and not by way of limitation, communication interface 1310 may include a network interface controller (NIC) or network adapter for communicating with an Ethernet or other wire-based network or a wireless NIC (WNIC) or wireless adapter for communicating with a wireless network, such as a WI-FI network. This disclosure contemplates any suitable network and any suitable communication interface 1310 for it. As an example and not by way of limitation, computer system 1300 may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, computer system 1300 may communicate with a wireless PAN (WPAN) (such as, for example, a BLUETOOTH WPAN), a WI-FI network, a WI-MAX network, a cellular telephone network (such as, for example, a Global System for Mobile Communications (GSM) network), or other suitable wireless network or a combination of two or more of these. Computer system 1300 may include any suitable communication interface 1310 for any of these networks, where appropriate. Communication interface 1310 may include one or more communication interfaces 1310, where appropriate. Although this disclosure describes and illustrates a particular communication interface, this disclosure contemplates any suitable communication interface.

In particular embodiments, bus 1312 includes hardware, software, or both coupling components of computer system 1300 to each other. As an example and not by way of limitation, bus 1312 may include an Accelerated Graphics Port (AGP) or other graphics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination of two or more of these. Bus 1312 may include one or more buses 1312, where appropriate. Although this disclosure describes and illustrates a particular bus, this disclosure contemplates any suitable bus or interconnect.

Herein, a computer-readable non-transitory storage medium or media may include one or more semiconductor-based or other integrated circuits (ICs) (such, as for example, field-programmable gate arrays (FPGAs) or application-specific ICs (ASICs)), hard disk drives (HDDs), hybrid hard drives (HHDs), optical discs, optical disc drives (ODDs), magneto-optical discs, magneto-optical drives, floppy diskettes, floppy disk drives (FDDs), magnetic tapes, solid-state drives (SSDs), RAM-drives, SECURE DIGITAL cards or drives, any other suitable computer-readable non-transitory storage media, or any suitable combination of two or more of these, where appropriate. A computer-readable non-transitory storage medium may be volatile, non-volatile, or a combination of volatile and non-volatile, where appropriate.

Herein, "or" is inclusive and not exclusive, unless expressly indicated otherwise or indicated otherwise by context. Therefore, herein, "A or B" means "A, B, or both," unless expressly indicated otherwise or indicated otherwise by context. Moreover, "and" is both joint and several, unless expressly indicated otherwise or indicated otherwise by context. Therefore, herein, "A and B" means "A and B, jointly or severally," unless expressly indicated otherwise or indicated otherwise by context.

The scope of this disclosure encompasses all changes, substitutions, variations, alterations, and modifications to the example embodiments described or illustrated herein that a person having ordinary skill in the art would comprehend. The scope of this disclosure is not limited to the example embodiments described or illustrated herein. Moreover, although this disclosure describes and illustrates respective embodiments herein as including particular components, elements, feature, functions, operations, or steps, any of these embodiments may include any combination or permutation of any of the components, elements, features, functions, operations, or steps described or illustrated anywhere herein that a person having ordinary skill in the art would comprehend. Furthermore, any reference herein to an apparatus or system or a component of an apparatus or system being adapted to, arranged to, capable of, configured to, enabled to, operable to, or operative to perform a particular function encompasses that apparatus, system, component, whether or not it or that particular function is activated, turned on, or unlocked, as long as that apparatus, system, or component is so adapted, arranged, capable, configured, enabled, operable, or operative. Additionally, although this disclosure describes or illustrates particular embodiments as providing particular advantages, particular embodiments may provide none, some, or all of these advantages.

The invention claimed is:

1. A method for evaluating player metrics comprising, by one or more computing devices of a sports operating system:
   accessing, by the one or more computing devices of the sports operating system, user sensor data from one or more wearable sensors on one or more players and optical sensor data from one or more cameras, wherein the user sensor data comprises location data of the player and acceleration data, and wherein the optical sensor data comprises a plurality of frames portraying the one or more players and a plurality of scenes from an athletic event;
   analyzing, by a machine-learning model of the sports operating system, the optical sensor data to identify the one or more players associated with the one or more wearable sensors and one or more actions during the athletic event;
   synchronizing, by the one or more computing devices of the sports operating system, the optical sensor data of the identified one or more players with user sensor data of the respective one or more wearable sensors on the identified one or more players using the analysis of the optical sensor data to identify the one or more players associated with the one or more wearable sensors and one or more actions during the athletic event;
   calculating, by the one or more computing devices of the sports operating system, one or more player metrics for the identified one or more players based on the synchronized user sensor data and the identified actions captured within the synchronized optical sensor data, wherein the one or more player metrics are based on a role associated with the identified one or more players;
   normalizing, using one or more benchmark algorithms of the sports operating system, the one or more player metrics for the one or more players based on one or more weighted parameters and one or more other player metrics corresponding to the one or more players having the same role associated with the identified one or more players;
   predicting, using one or more performance evaluation algorithms of the sports operating system, one or more future outcome and one or more performance levels for the one or more players based on their associated roles; and
   providing, by the one or more computing devices of the sports operating system, a report to one or more users about the one or more normalized player metrics and the one or more future outcomes and the one or more performance levels for the one or more players.

2. The method of claim 1, further comprising:
   receiving feedback related to the one or more players or the one or more actions; and
   updating the machine-learning model based on the feedback corresponding to the one or more players or the one or more actions.

3. The method of claim 1, wherein the wearable sensors are configured as one or more of a wearable buckle, a waist band clip, a wearable boot, a boxing glove style sensor, or a body patch.

4. The method of claim 1, wherein the user sensor data and the optical sensor data is accessed in real-time as the athletic event occurs, and wherein the wearable sensors comprise cellular antennas.

5. The method of claim 1, further comprising:
   determining whether the one or more users have permission from the first player to access the report, wherein the report is provided to the one or more users in response to determining the one or more users have permission from the one or more players to access the report.

6. The method of claim 1, further comprising:
   accessing one or more player goals for the one or more players; and
   tracking the one or more player goals for the one or more players based on the one or more normalized player metrics, wherein the report indicates a progress on completing the one or more player goals for the one or more players.

7. The method of claim 1, further comprising:
accessing one or more third-party data sources, wherein the calculation of the one or more player metrics is further based on the one or more third-party data sources.

8. The method of claim 1, further comprising:
accessing data indicative of one or more prior athletic events, wherein the calculation of the one or more player metrics is further based on the data indicative of the one or more prior athletic events, and wherein the prediction of the one or more future outcomes is further based on the data indicative of the one or more prior athletic events.

9. The method of claim 1, further comprising:
accessing data indicative of one or more behavioral actions of the identified one or more players, wherein the calculation of the one or more player metrics is further based on the data indicative of the one or more behavioral actions, and wherein the prediction of the one or more future outcomes is further based on the data indicative of the one or more behavioral actions of the identified one or more players.

10. The method of claim 9, wherein the data indicative of the one or more behavioral actions comprises one or more of financial data, sleep data, or nutrition data.

11. The method of claim 1, wherein the report to the one or more users further includes one or more training strategies for the identified one or more players, wherein the one or more training strategies are for one or more of a player development, a player valuation, or a health safety of the identified one or more players.

12. The method of claim 1, wherein the athletic event is associated with a first sport of a plurality of sports, wherein the normalization of the one or more player metrics is based on the first sport of the plurality of sports.

13. The method of claim 1, further comprising:
generating a valuation of the identified one or more players based on the one or more normalized player metrics, wherein the report comprises the valuation.

14. A sports operating system for evaluating player metrics comprising:
one or more processors; and
one or more computer-readable non-transitory storage media coupled to one or more of the processors and comprising instructions operable when executed by one or more of the processors to cause the system to:
access user sensor data from one or more wearable sensors on one or more players and optical sensor data from one or more cameras, wherein the user sensor data comprises location data of the player and acceleration data, and wherein the optical sensor data comprises a plurality of frames portraying the one or more players and a plurality of scenes from an athletic event;
analyze, by a machine-learning model of the sports operating system, the optical sensor data to identify the one or more players associated with the one or more wearable sensors and one or more actions during the athletic event;
synchronize the optical sensor data of the identified one or more players with user sensor data of the respective one or more wearable sensors on the identified one or more players using the analysis of the optical sensor data to identify the one or more players associated with the one or more wearable sensors and one or more actions during the athletic event;
calculate one or more player metrics for the identified one or more players based on the synchronized user sensor data and the identified actions captured within the synchronized optical sensor data, wherein the one or more player metrics are based on a role associated with the identified one or more players;
normalize, using one or more benchmark algorithms of the sports operating system, the one or more player metrics for the one or more players based on one or more weighted parameters and one or more other player metrics corresponding to the one or more players having the same role associated with the identified one or more players;
predict, using one or more performance evaluation algorithms of the sports operating system, one or more future outcome and one or more performance levels for the one or more players based on their associated roles; and
provide a report to one or more users about the one or more normalized player metrics and the one or more future outcomes and the one or more performance levels for the one or more players.

15. The sports operating system of claim 14, wherein the instructions are further operable when executed by one or more of the processors to cause the sports operating system to:
receive feedback related to the one or more players or the one or more actions; and
update the machine-learning model based on the feedback corresponding to the one or more players or the one or more actions.

16. The sports operating system of claim 14, wherein the wearable sensors are configured as one or more of a wearable buckle, a waist band clip, a wearable boot, a boxing glove style sensor, or a body patch.

17. The sports operating system of claim 14, wherein the user sensor data and the optical sensor data is accessed in real-time as the athletic event occurs, and wherein the wearable sensors comprise cellular antennas.

18. The sports operating system of claim 14, wherein the instructions are further operable when executed by one or more of the processors to cause the system to:
determine whether the one or more users have permission from the first player to access the report, wherein the report is provided to the one or more users in response to determining the one or more users have permission from the one or more players to access the report.

19. The sports operating system of claim 14, wherein the instructions are further operable when executed by one or more of the processors to cause the system to:
access one or more player goals for the one or more players; and
track the one or more player goals for the one or more players based on the one or more normalized player metrics, wherein the report indicates a progress on completing the one or more player goals for the one or more players.

20. One or more computer-readable non-transitory storage media embodying software for evaluating player metrics that is operable when executed by one or more processors of a sports operating system to:
access user sensor data from one or more wearable sensors on one or more players and optical sensor data from one or more cameras, wherein the user sensor data comprises location data of the player and acceleration data, and wherein the optical sensor data comprises a plurality of frames portraying the one or more players and a plurality of scenes from an athletic event;

analyze, by a machine-learning model of the sports operating system, the optical sensor data to identify the one or more players associated with the one or more wearable sensors and one or more actions during the athletic event;

synchronize the optical sensor data of the identified one or more players with user sensor data of the respective one or more wearable sensors on the identified one or more players using the analysis of the optical sensor data to identify the one or more players associated with the one or more wearable sensors and one or more actions during the athletic event;

calculate one or more player metrics for the identified one or more players based on the synchronized user sensor data and the identified actions captured within the synchronized optical sensor data, wherein the one or more player metrics are based on a role associated with the identified one or more players;

normalize, using one or more benchmark algorithms of the sports operating system, the one or more player metrics for the one or more players based on one or more weighted parameters and one or more other player metrics corresponding to the one or more players having the same role associated with the identified one or more players;

predict, using one or more performance evaluation algorithms of the sports operating system, one or more future outcome and one or more performance levels for the one or more players based on their associated roles; and provide a report to one or more users about the one or more normalized player metrics and the one or more future outcomes and the one or more performance levels for the one or more players.

* * * * *